United States Patent
Rotolo et al.

(10) Patent No.: US 10,722,577 B2
(45) Date of Patent: Jul. 28, 2020

(54) METHODS FOR TREATING GI SYNDROME AND GRAFT VERSUS HOST DISEASE

(71) Applicant: Sloan Kettering Institute for Cancer Research, New York, NY (US)

(72) Inventors: Jimmy Andrew Rotolo, Port Washington, NY (US); Richard N. Kolesnick, New York, NY (US)

(73) Assignee: Sloan Kettering Institute for Cancer Research, New York, NY (US)

( * ) Notice: Subject to any disclaimer, the term of this patent is extended or adjusted under 35 U.S.C. 154(b) by 301 days.

(21) Appl. No.: 14/402,875

(22) PCT Filed: May 28, 2013

(86) PCT No.: PCT/US2013/042941
§ 371 (c)(1),
(2) Date: Nov. 21, 2014

(87) PCT Pub. No.: WO2013/177596
PCT Pub. Date: Nov. 28, 2013

(65) Prior Publication Data
US 2015/0216971 A1    Aug. 6, 2015

Related U.S. Application Data

(60) Provisional application No. 61/651,729, filed on May 25, 2012.

(51) Int. Cl.
| | | |
|---|---|---|
| A61K 39/00 | (2006.01) | |
| A61K 39/395 | (2006.01) | |
| A61K 45/06 | (2006.01) | |
| A61K 31/496 | (2006.01) | |
| A61K 31/55 | (2006.01) | |
| C07K 16/44 | (2006.01) | |
| A61K 31/4709 | (2006.01) | |
| C07K 16/18 | (2006.01) | |

(52) U.S. Cl.
CPC .... *A61K 39/39533* (2013.01); *A61K 31/4709* (2013.01); *A61K 31/496* (2013.01); *A61K 31/55* (2013.01); *A61K 39/39541* (2013.01); *A61K 45/06* (2013.01); *C07K 16/18* (2013.01); *C07K 16/44* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| | | |
|---|---|---|
| 4,950,649 A | 8/1990 | Rineheart |
| 5,331,093 A | 7/1994 | Ishihara et al. |
| 5,877,293 A | 3/1999 | Adair et al. |
| 5,886,152 A | 3/1999 | Nakatani et al. |
| 6,054,297 A | 4/2000 | Carter et al. |
| 7,812,015 B2 | 10/2010 | Gulbins |
| 2003/0165835 A1 | 9/2003 | Spies et al. |
| 2003/0190715 A1 | 10/2003 | Grosse et al. |
| 2004/0109855 A1 | 6/2004 | Waldmann et al. |
| 2005/0209219 A1 | 9/2005 | Gulbins |
| 2007/0237752 A1* | 10/2007 | Christensen ........... A61K 35/15  424/93.7 |
| 2010/0183749 A1* | 7/2010 | Brey .................... A61K 31/573  424/715 |
| 2010/0239572 A1* | 9/2010 | Rotolo .................. C07K 16/28  424/133.1 |

FOREIGN PATENT DOCUMENTS

| | | |
|---|---|---|
| JP | 2006-505527 A | 2/2006 |
| JP | 2010-526153 A | 7/2010 |
| KR | 20050014573 A | 2/2005 |
| WO | 2005025489 A2 | 3/2005 |
| WO | 2006133450 A2 | 12/2006 |
| WO | 2008/137901 A2 | 11/2008 |
| WO | 2008137901 A9 | 4/2009 |

OTHER PUBLICATIONS

Grassme, H., et al., "CD95 Signaling via Ceramide-rich Membrane Rafts", Journal of Biological Chemistry, 2001, pp. 20589-20596, vol. 276, No. 23, Publisher: The American Society for Biochemistry and Molecular Biology, Inc.
Gulbins, E., and Kolesnick, R., "Raft ceramide in molecular medicine", Oncogene 2003, pp. 7070-7077, vol. 22, Publisher: Nature Publishing Group.
Kolesnick, R. and Fuks, Z., "Ceramide: a signal for apoptosis or mitogenesis?," J. Exp. Med. 1995, pp. 1949-1952, vol. 181, No. 6.
Novack, V., et al., "Do statins have a role in preventing or treating sepsis?," Critical Care 2006, pp. 1-3, vol. 10, No. 113, DOI: 10.1186/cc3972, Publisher: BioMed Central Ltd.
Oliva-Hemker, M., et al., Pernicious anemia and widespread absence of gastrointestinal endocrine cells in a patient with autoimmune polyglandular syndrome type I and malabsorption, The Journal of Clinical Endocrinology & Metabolism 2006, pp. 2833-2838, vol. 91, No. 8, Publisher: The Endocrine Society.
Petersen, N.H., et al., "Transformation-associated changes in sphingolipid metabolism sensitize cells to lysosomal cell death induced by inhibitors of acid sphingomyelinase," Cancer Cell 2013, pp. 379-393, vol. 24, No. 3, DOI: 10.1016/j.ccr.2013.08.003, Publisher: Elsevier Inc.
Rotolo, J., et al., "Caspase-dependent and -independent Activation of Acid Sphingomyelinase Signaling," The Journal of Biological Chemistry 2005, pp. 26425-26434, vol. 280, No. 28, DOI: 10.1074/jbc.M414569200, Publisher: The American Society for Biochemistry and Molecular Biology, Inc.

(Continued)

Primary Examiner — Lei Yao
(74) Attorney, Agent, or Firm — Foley & Lardner LLP

(57) ABSTRACT

It has been discovered that administering therapeutically effective amounts of an antibiotic that kills Gram-negative bacteria, together with an anti-ceramide antibody or anti-ceramide mimetic, treats and prevents an array of diseases mediated by cytolytic T lymphocyte (CTL)-induced killing and/or by damage to endothelial microvasculature, including Radiation GI syndrome, GvHD disease, inflammatory diseases and autoimmune diseases.

9 Claims, 13 Drawing Sheets

Specification includes a Sequence Listing.

(56) References Cited

OTHER PUBLICATIONS

Stage, K.B., et al., "Depression in COPD—management and quality of life considerations," International Journal of COPD 2006, pp. 315-320, vol. 1, No. 3, Publisher: Dove Medical Press Limited.
Stancevic, B. and Kolesnick, R., "Ceramide-rich platforms in transmembrane signaling," FEBS Lett. 2010, pp. 1728-1740, vol. 584, No. 9, DOI: 10.1016/j.febslet.2010.02.026.
Suit, H.D., and Willers, H., "Comment on Tumor Response to Radiotherapy Regulated by Endothelial Cell Apoptosis," Science 2003, p. 1894c, vol. 302.
Vielhaber, G., et al., "Mouse anti-ceramide antiserum: a specific tool for the detection of endogenous ceramide," Glycobiology 2011, pp. 451-457, vol. 11, No. 6.
CIPO: Office Action, Canadian Patent Application No. 2,686,722, dated Jul. 30, 2013, pp. 1-4.
CIPO: Office Action, Canadian Patent Application No. 2,686,722, dated Nov. 28, 2014, pp. 1-5.
EPO: Office Action, European Patent Application No. 08755086.9, dated Apr. 25, 2012, pp. 1-8.
IP Australia: Patent Examination Report, Australian Patent Application No. 2008247368, dated Aug. 31, 2012, pp. 1-8.
ISA/US: International Search Report and Written Opinion, International Patent Application No. PCT/US08/62789, dated Oct. 7, 2008, pp. 1-15.
JPO: Notice of Reasons for Refusal Japanese Patent Application No. 507601/2010, dated Jan. 8, 2013, pp. 1-5.
JPO: Decision of Refusal, Japanese Patent Application No. 507601/2010, dated Jan. 21, 2014, pp. 1-3.
JPO: Notice of Reasons for Refusal, Appeal of Japanese Patent Application No. 507601/2010, dated Jun. 30, 2015, pp. 1-7.
CIPO, "Official Action for the corresponding Canadian application # 2686722", Dec. 10, 2015, pp. 1-6, Publisher: Canadian Intellectual Property Office, Published in: www.cipo.gc.ca.
Gulbins, E. et al., "Physiological and pathophysiological aspects of ceramide," Am J Physiol Regul Integr Comp Physiol, 290, pp. R11-R26, 2006, Published in: http://ajpreg.org.
EPO, "Supplementary Search Report for the corresponding European application EP13793069", Dec. 7, 2015, pp. 1-11, Publisher: EPO.
Fan, Xiaohui, et al., "Construction and expression of 2A2 chimeric antibody 2A2 neutralising cathepsin B activity", "Anticancer Research—International Journal of Cancer Research and Treatment", 2002, p. 4322, vol. 22, No. 6C, Publisher: International Institute of Anticancer Research, Published in: Highlands, NJ.
Mueller, J. P., et al., "Humanized porcine VCAM-specific monoclonal antibodies with chimeric igG2/G4 constant regions block human leukocyte binding to porcine endothelial cells", "Molecular Immunology", 1997, pp. 441-452, vol. 34, No. 6, Publisher: Pergamon, Published in: doi: 10.1016/S0161-5890(97)00042-4.
Rotolo, Jimmy, et al., "Anti-ceramide antibody prevents the radiation gastrointestinal syndrome in mice", "J Clin Invest", 2012, pp. 1786-1790, vol. 122, No. 5, Publisher: American Society for Clinical Investigation, Published in: doi: 10.1172/JCI59920.
ISA/US, "International Search Report and Written Opinion for the corresponding PCT application US2013/042941", dated Dec. 23, 2013, pp. 1-12.
Office Action, Japanese Patent Application No. 256345/2015, dated Oct. 4, 2016, 7 pages.
Cowart, L.A, et al., "Structural determinants of sphingolipid recognition by commercially available anti-ceramide antibodies," Journal of Lipid Research 2002, pp. 2042-2048, vol. 43, Publisher: Lipid Research, Inc.
Kawase, M., et al., "Increase of ceramide in adriamycin-induced HL-60 cell apoptosis: detection by a novel anti-ceramide antibody," Biochimica et Biophysica Acta 2002, pp. 104-114, vol. 1584, Publisher: Elsevier Science B.V.
Krishnamurthy, K., et al., "Development and characterization of a novel anti-ceramide antibody," Journal of Lipid Research 2007, pp. 968-975, vol. 48, Publisher: American Society for Biochemistry and Molecular Biology, Inc.
Paris, F., et al., "Endothelial Apoptosis as the Primary Lesion Initiating Intestinal Radiation Damage in Mice," Science 2001, pp. 293-297, vol. 293.
Vielhaber, G., et al., "Endothelial Apoptosis as the Primary Lesion Initiating Intestinal Radiation Damage in Mice," Glycobiology 2001, pp. 451-457, vol. 11, No. 6, Publisher: Oxford University Press.
English-language translation of Decision of Refusal, Japanese Patent App. No. 2015-214243, Sloan Kettering Institute for Cancer Research, 4 pages (Jun. 6, 2017).
ISA/JPO: Notice of Reasons for Refusal, Japanese Patent Application No. 514243/2015, dated Feb. 21, 2017, 12 pages.
Kim, K., et al., "High-throughput screening identifies two classes of antibiotics as radioprotectors: tetracyclines and fluoroquinolones," Clin Cancer Res. 2009, pp. 7238-7245, DOI: 10.1158/1078-0432. CCR-09-1964, Publisher: American Association for Cancer Research.
Shalit, I., et al., "Enhanced hematopoiesis in sublethally irradiated mice treated with various quinolones," Eur J Haematol. 1997, pp. 92-98, vol. 58, Publisher: Munksguard.
Tamaoka, A., "Passive Immunization in Neurological Disorders," Journal of Clinical and Experimental Medicine 2011, pp. 738-743, vol. 238, No. 6.
Lozano et al., "Cell autonomous apoptosis defects in acid sphingomyelinase knockout fibroblasts," J. Biol. Chem., vol. 276, No. 1, pp. 442-448 (Oct. 2000).

* cited by examiner

Mitigation effect of 2A2 Ab (SBI 15.5 Gy)

Mitigation effect of Oral Antibiotic

Humanized h2A2 Ab Preferentially Binds to Ceramide

Humanized 2A2 Ab Displays Superior Binding to Ceramide Compared to Mouse 2A2 Ab

Humanized 2A2 Ab Inhibits Jurkat Cell Apoptosis

Humanized 2A2 Ab Improves Crypt Stem Cell Survival Following Lethal Radiation Exposure

Humanized 2A2 Ab Protects Crypt Stem Cells

Humanized 2A2 Ab is an Effective Radioprotector or Mitigator When Administered Via Intraperitoneal Injection

Humanized 2A2 Ab Protects Animals From Lethal RGS

SEQUENCE LISTING

<160> NUMBER OF SEQ ID NOS: 15

<210> SEQ ID NO 1
<211> LENGTH: 115
<212> TYPE: PRT
<213> ORGANISM: Mouse sp.
<220> FEATURE:
<223> OTHER INFORMATION: Mouse 2A2 Variable Heavy Chain (VH)

<400> SEQUENCE: 1

Glu Val Gln Leu Gln Gln Ser Gly Thr Val Leu Ala Arg Pro Gly Ala

```
                 1               5                  10                 15
            Ser Val Lys Met Ser Cys Lys Ala Ser Gly Tyr Thr Phe Thr Asn Tyr
                         20                  25                 30

Trp Met His Trp Val Lys Gln Arg Pro Val Gln Gly Leu Glu Trp Ile
                         35                  40                 45

Gly Ala Ile Tyr Pro Gly Asp Ser Asp Thr Ser Tyr Asn Gln Lys Phe
                         50                  55                 60

Lys Gly Lys Ala Lys Leu Thr Ala Val Thr Ser Thr Ser Thr Ala Phe
             65                  70                  75                 80

Met Glu Leu Ser Ser Leu Thr Asn Glu Asp Ser Ala Val Tyr Tyr Cys
                         85                  90                 95

Thr Gly Leu Tyr Tyr Gly Tyr Asp Trp Gly Gln Gly Thr Thr Leu Thr
                         100                 105                110

Val Ser Ser
                         115

<210> SEQ ID NO 2
<211> LENGTH: 109
<212> TYPE: PRT
<213> ORGANISM: Homo sapiens
<220> FEATURE:
<223> OTHER INFORMATION: Human germline 2A2 Variable Heavy Chain of the
      2A2 antibody

<400> SEQUENCE: 2

Gln Val Gln Leu Val Gln Ser Gly Ala Glu Val Lys Lys Pro Gly Ala
             1               5                  10                 15

Ser Val Lys Val Ser Cys Lys Ala Ser Gly Tyr Thr Phe Thr Ser Tyr
                         20                  25                 30

Tyr Met His Trp Val Arg Gln Ala Pro Gly Gln Gly Leu Glu Trp Met
                         35                  40                 45

Gly Ile Ile Asn Pro Ser Gly Gly Ser Thr Ser Tyr Ala Gln Lys Phe
                         50                  55                 60

Gln Gly Arg Val Thr Met Thr Arg Asp Thr Ser Thr Ser Thr Val Tyr
             65                  70                  75                 80

Met Glu Leu Ser Ser Leu Arg Ser Glu Asp Thr Ala Val Tyr Tyr Cys
                         85                  90                 95

Ala Arg Trp Gly Gln Gly Thr Thr Val Thr Val Ser Ser
                         100                 105

<210> SEQ ID NO 3
<211> LENGTH: 112
<212> TYPE: PRT
<213> ORGANISM: Mouse sp.
<220> FEATURE:
<223> OTHER INFORMATION: Mouse 2A2 Variable Light Chain (VL)

<400> SEQUENCE: 3

Asp Val Leu Met Thr Gln Thr Pro Leu Thr Leu Ser Val Thr Ile Gly
             1               5                  10                 15

Gln Pro Ala Ser Ile Ser Cys Lys Ser Ser Gln Ser Leu Ile Asp Ser
                         20                  25                 30

Asp Gly Lys Thr Phe Leu Asn Trp Leu Leu Gln Arg Pro Gly Gln Ser
                         35                  40                 45

Pro Lys Arg Leu Ile Tyr Leu Val Ser Lys Leu Asp Ser Gly Val Pro
             50                  55                  60

Asp Arg Phe Thr Gly Ser Gly Ser Gly Thr Asp Phe Thr Leu Lys Ile
             65                  70                  75                 80
```

Ser Arg Val Glu Ala Glu Asp Leu Gly Leu Tyr Tyr Cys Trp Gln Gly
            85                  90                  95

Thr His Phe Pro Tyr Thr Phe Gly Gly Gly Thr Lys Leu Glu Ile Lys
            100                 105                 110

<210> SEQ ID NO 4
<211> LENGTH: 112
<212> TYPE: PRT
<213> ORGANISM: Homo sapiens
<220> FEATURE:
<223> OTHER INFORMATION: Human germline 2A2 Variable Light (VL)

<400> SEQUENCE: 4

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
            85                  90                  95

Thr His Trp Pro Thr Phe Gly Gln Gly Thr Lys Leu Glu Ile Lys Arg
            100                 105                 110

<210> SEQ ID NO 5
<211> LENGTH: 1395
<212> TYPE: DNA
<213> ORGANISM: Artificial Sequence
<220> FEATURE:
<223> OTHER INFORMATION: Description of Artificial Sequence: Synthetic
      humanized 2a2 heavy chain sequence

<400> SEQUENCE: 5
atggactgga cctggagggt cttctgcttg ctggctgtag ctccaggtgc tcactcccag      60
gtgcagcttg tgcagtctgg ggctgaggtg aaaaagcctg ggcttcagt gaaggtgtcc      120 tgcaaggctt ctggctacac ctttaccaac tactggatgc actgggtaag acaggcgcct     180
ggacagggtc tggaatggat gggcgctatt tatcctggag atagtgatac tagctacaac     240
cagaagttca gggccgggt cacaatgact cgagacacat ccaccagcac tgtctacatg      300
gagctcagca gcctgagaag tgaggacact gcggtctatt actgtgcacg cctttactac     360
ggctacgact ggggccaagg caccactgtc acagtctcct cagccagcac gaagggccca     420
tcggtcttcc ccctggcacc ctcctccaag agcacctctg ggggcacagc ggccctgggc     480
tgcctggtca aggactactt ccccgaaccg gtgacggtgt cgtggaactc aggcgccctg     540
accagcggcg tgcacacctt cccggctgtc ctacagtcct caggactcta ctccctcagc     600
agcgtggtga ccgtgccctc agcagcttg ggcacccaga cctacatctg caacgtgaat     660
cacaagccca gcaacaccaa ggtggacaag aaagttgagc ccaaatcttg tgacaaaact     720
cacacatgcc caccgtgccc agcacctgaa ctcctggggg gaccgtcagt cttcctcttc     780 ccccaaaac ccaaggacac cctcatgatc tcccggaccc ctgaggtcac atgcgtggtg      840
gtggacgtga gccacgaaga ccctgaggtc aagttcaact ggtacgtgga cggcgtggag     900

```
gtgcataatg ccaagacaaa gccgcgggag gagcagtaca acagcacgta ccgtgtggtc   960
agcgtcctca ccgtcctgca ccaggactgg ctgaatggca aggagtacaa gtgcaaggtc  1020
tccaacaaag ccctcccagc ccccatcgag aaaaccatct ccaaagccaa agggcagccc  1080
cgagaaccac aggtgtacac cctgccccca tcccgggatg agctgaccaa gaaccaggtc  1140
agcctgacct gcctggtcaa aggcttctat cccagcgaca tcgccgtgga gtgggagagc  1200
aatgggcagc cggagaacaa ctacaagacc acgcctcccg tgctggactc cgacggctcc  1260
ttcttcctct acagcaagct caccgtggac aagagcaggt ggcagcaggg gaacgtcttc  1320
tcatgctccg tgatgcatga ggctctgcac aaccactaca cgcagaagag cctctccctg  1380
tccccgggta aatga                                                   1395
```

<210> SEQ ID NO 6
<211> LENGTH: 463
<212> TYPE: PRT
<213> ORGANISM: Artificial Sequence
<220> FEATURE:
<223> OTHER INFORMATION: Description of Artificial Sequence: Synthetic humanized 2a2 heavy chain sequence

<400> SEQUENCE: 6

```
Met Asp Trp Thr Trp Arg Val Phe Cys Leu Leu Ala Val Ala Pro Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Trp Met His Trp Val Arg Gln Ala Pro Gly Gln Gly Leu
    50                  55                  60

Glu Trp Met Gly Ala Ile Tyr Pro Gly Asp Ser Asp Thr Ser Tyr Asn
65                  70                  75                  80

Gln Lys Phe Lys Gly Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Leu Tyr Tyr Gly Tyr Asp Trp Gly Gln Gly Thr
        115                 120                 125

Thr Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270
```

```
            Thr Pro Glu Val Thr Cys Val Val Asp Val Ser His Glu Asp Pro
                275                 280                 285

Glu Val Lys Phe Asn Trp Tyr Val Asp Gly Val Glu Val His Asn Ala
            290                 295                 300

Lys Thr Lys Pro Arg Glu Glu Gln Tyr Asn Ser Thr Tyr Arg Val Val
            305                 310                 315                 320

Ser Val Leu Thr Val Leu His Gln Asp Trp Leu Asn Gly Lys Glu Tyr
                            325                 330                 335

Lys Cys Lys Val Ser Asn Lys Ala Leu Pro Ala Pro Ile Glu Lys Thr
                        340                 345                 350

Ile Ser Lys Ala Lys Gly Gln Pro Arg Glu Pro Gln Val Tyr Thr Leu
                    355                 360                 365

Pro Pro Ser Arg Asp Glu Leu Thr Lys Asn Gln Val Ser Leu Thr Cys
                370                 375                 380

Leu Val Lys Gly Phe Tyr Pro Ser Asp Ile Ala Val Glu Trp Glu Ser
            385                 390                 395                 400

Asn Gly Gln Pro Glu Asn Asn Tyr Lys Thr Thr Pro Pro Val Leu Asp
                            405                 410                 415

Ser Asp Gly Ser Phe Phe Leu Tyr Ser Lys Leu Thr Val Asp Lys Ser
                        420                 425                 430

Arg Trp Gln Gln Gly Asn Val Phe Ser Cys Ser Val Met His Glu Ala
                    435                 440                 445

Leu His Asn His Tyr Thr Gln Lys Ser Leu Ser Leu Ser Pro Gly
                450                 455                 460

<210> SEQ ID NO 7
<211> LENGTH: 720
<212> TYPE: DNA
<213> ORGANISM: Artificial Sequence
<220> FEATURE:
<223> OTHER INFORMATION: Description of Artificial Sequence: Synthetic
      humanized 2a2 light chain sequence

<400> SEQUENCE: 7
atgaggctcc ctgctcagct cctggggctg ctaatgctct gggtcccagg atccagtggg    60
gatgttgtga tgacccaatc tccactctct ttgccggtta cccttggaca accagcctcc   120
atctcttgca gtcaagtca gagcctcata gatagtgatg aaagacatt tttgaattgg     180 ttccaacaga ggccaggcca gtctccaagg cgcctaatct atctggtgtc taaactggac   240
tctggagtcc ctgacaggtt ctctggcagt ggatcaggga cagatttcac tctgaaaatc   300
agcagagtgg aggctgagga tgtgggagtt tattattgct ggcaaggtac acattttccg   360
tacacgttcg gacaggggac caagctggaa ataaaacgga cggtggctgc accatctgtc   420
ttcatcttcc cgccatctga tgagcagttg aaatctggaa ctgcctctgt tgtgtgcctg   480
ctgaataact tctatcccag agaggccaaa gtacagtgga aggtggataa cgccctccaa   540
tcgggtaact cccaggagag tgtcacagag caggacagca aggacagcac ctacagcctc   600
agcagcaccc tgacgctgag caaagcagac tacgagaaac acaaagtcta cgcctgcgaa   660
gtcacccatc agggcctgag ttcgcccgtc acaaagagct tcaacagggg agagtgttaa   720

<210> SEQ ID NO 8
<211> LENGTH: 239
<212> TYPE: PRT
<213> ORGANISM: Artificial Sequence
<220> FEATURE:
<223> OTHER INFORMATION: Description of Artificial Sequence: Synthetic
``` humanized 2a2 light chain sequence

<400> SEQUENCE: 8

Met Arg Leu Pro Ala Gln Leu Leu Gly Leu Leu Met Leu Trp Val Pro
1               5                   10                  15

Gly Ser Ser Gly Asp Val Val Met Thr Gln Ser Pro Leu Ser Leu Pro
                20                  25                  30

Val Thr Leu Gly Gln Pro Ala Ser Ile Ser Cys Lys Ser Ser Gln Ser
            35                  40                  45

Leu Ile Asp Ser Asp Gly Lys Thr Phe Leu Asn Trp Phe Gln Gln Arg
    50                  55                  60

Pro Gly Gln Ser Pro Arg Arg Leu Ile Tyr Leu Val Ser Lys Leu Asp
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Trp Gln Gly Thr His Phe Pro Tyr Thr Phe Gly Gln Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

```
<210> SEQ ID NO 9
<211> LENGTH: 115
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Glu or Gln
<220> FEATURE:
<221> NAME/KEY: MOD_RES
<222> LOCATION: (5)..(5)
<223> OTHER INFORMATION: Gln or Val
<220> FEATURE:
<221> NAME/KEY: MOD_RES
<222> LOCATION: (9)..(9)
<223> OTHER INFORMATION: Thr or Ala
<220> FEATURE:
<221> NAME/KEY: MOD_RES
<222> LOCATION: (10)..(10)
<223> OTHER INFORMATION: Val or Glu
<220> FEATURE:
<221> NAME/KEY: MOD_RES
<222> LOCATION: (11)..(11)
<223> OTHER INFORMATION: Leu or Val
<220> FEATURE:
<221> NAME/KEY: MOD_RES
```

```
<222> LOCATION: (12)..(12)
<223> OTHER INFORMATION: Ala or Lys
<220> FEATURE:
<221> NAME/KEY: MOD_RES
<222> LOCATION: (13)..(13)
<223> OTHER INFORMATION: Arg or Lys
<220> FEATURE:
<221> NAME/KEY: MOD_RES
<222> LOCATION: (20)..(20)
<223> OTHER INFORMATION: Met or Val
<220> FEATURE:
<221> NAME/KEY: MOD_RES
<222> LOCATION: (31)..(31)
<223> OTHER INFORMATION: Asn or Ser
<220> FEATURE:
<221> NAME/KEY: MOD_RES
<222> LOCATION: (33)..(33)
<223> OTHER INFORMATION: Trp or Tyr
<220> FEATURE:
<221> NAME/KEY: MOD_RES
<222> LOCATION: (38)..(38)
<223> OTHER INFORMATION: Lys or Arg
<220> FEATURE:
<221> NAME/KEY: MOD_RES
<222> LOCATION: (40)..(40)
<223> OTHER INFORMATION: Arg or Ala
<220> FEATURE:
<221> NAME/KEY: MOD_RES
<222> LOCATION: (42)..(42)
<223> OTHER INFORMATION: Val or Gly
<220> FEATURE:
<221> NAME/KEY: MOD_RES
<222> LOCATION: (48)..(48)
<223> OTHER INFORMATION: Ile or Met
<220> FEATURE:
<221> NAME/KEY: MOD_RES
<222> LOCATION: (50)..(50)
<223> OTHER INFORMATION: Ala or Ile
<220> FEATURE:
<221> NAME/KEY: MOD_RES
<222> LOCATION: (52)..(52)
<223> OTHER INFORMATION: Tyr or Asn
<220> FEATURE:
<221> NAME/KEY: MOD_RES
<222> LOCATION: (54)..(54)
<223> OTHER INFORMATION: Gly or Ser
<220> FEATURE:
<221> NAME/KEY: MOD_RES
<222> LOCATION: (55)..(55)
<223> OTHER INFORMATION: Asp or Gly
<220> FEATURE:
<221> NAME/KEY: MOD_RES
<222> LOCATION: (56)..(56)
<223> OTHER INFORMATION: Ser or Gly
<220> FEATURE:
<221> NAME/KEY: MOD_RES
<222> LOCATION: (57)..(57)
<223> OTHER INFORMATION: Asp or Ser
<220> FEATURE:
<221> NAME/KEY: MOD_RES
<222> LOCATION: (61)..(61)
<223> OTHER INFORMATION: Asn or Ala
<220> FEATURE:
<221> NAME/KEY: MOD_RES
<222> LOCATION: (65)..(65)
<223> OTHER INFORMATION: Lys or Gln
<220> FEATURE:
<221> NAME/KEY: MOD_RES
<222> LOCATION: (67)..(67)
<223> OTHER INFORMATION: Lys or Arg
<220> FEATURE:
<221> NAME/KEY: MOD_RES
<222> LOCATION: (68)..(68)
<223> OTHER INFORMATION: Ala or Val
<220> FEATURE:
<221> NAME/KEY: MOD_RES
<222> LOCATION: (69)..(69)
<223> OTHER INFORMATION: Lys or Thr
<220> FEATURE:
```

<220> FEATURE:
<221> NAME/KEY: MOD_RES
<222> LOCATION: (70)..(70)
<223> OTHER INFORMATION: Leu or Met
<220> FEATURE:
<221> NAME/KEY: MOD_RES
<222> LOCATION: (72)..(72)
<223> OTHER INFORMATION: Ala or Arg
<220> FEATURE:
<221> NAME/KEY: MOD_RES
<222> LOCATION: (73)..(73)
<223> OTHER INFORMATION: Val or Asp
<220> FEATURE:
<221> NAME/KEY: MOD_RES
<222> LOCATION: (79)..(79)
<223> OTHER INFORMATION: Ala or Val
<220> FEATURE:
<221> NAME/KEY: MOD_RES
<222> LOCATION: (80)..(80)
<223> OTHER INFORMATION: Phe or Tyr
<220> FEATURE:
<221> NAME/KEY: MOD_RES
<222> LOCATION: (87)..(87)
<223> OTHER INFORMATION: Thr or Arg
<220> FEATURE:
<221> NAME/KEY: MOD_RES
<222> LOCATION: (88)..(88)
<223> OTHER INFORMATION: Asn or Ser
<220> FEATURE:
<221> NAME/KEY: MOD_RES
<222> LOCATION: (91)..(91)
<223> OTHER INFORMATION: Ser or Thr
<220> FEATURE:
<221> NAME/KEY: MOD_RES
<222> LOCATION: (97)..(97)
<223> OTHER INFORMATION: Thr or Ala
<220> FEATURE:
<221> NAME/KEY: MOD_RES
<222> LOCATION: (98)..(98)
<223> OTHER INFORMATION: Gly or Arg
<220> FEATURE:
<221> NAME/KEY: MOD_RES
<222> LOCATION: (99)..(104)
<223> OTHER INFORMATION: May or may not be present
<220> FEATURE:
<221> NAME/KEY: MOD_RES
<222> LOCATION: (111)..(111)
<223> OTHER INFORMATION: Leu or Val

<400> SEQUENCE: 9

```
Xaa Val Gln Leu Xaa Gln Ser Gly Xaa Xaa Xaa Xaa Pro Gly Ala
1               5                   10                  15

Ser Val Lys Xaa Ser Cys Lys Ala Ser Gly Tyr Thr Phe Thr Xaa Tyr
            20                  25                  30

Xaa Met His Trp Val Xaa Gln Xaa Pro Xaa Gln Gly Leu Glu Trp Xaa
        35                  40                  45

Gly Xaa Ile Xaa Pro Xaa Xaa Xaa Xaa Thr Ser Tyr Xaa Gln Lys Phe
    50                  55                  60

Xaa Gly Xaa Xaa Xaa Xaa Thr Xaa Xaa Thr Ser Thr Ser Thr Xaa Xaa
65                  70                  75                  80

Met Glu Leu Ser Ser Leu Xaa Xaa Glu Asp Xaa Ala Val Tyr Tyr Cys
                85                  90                  95

Xaa Xaa Leu Tyr Tyr Gly Tyr Asp Trp Gly Gln Gly Thr Thr Xaa Thr
            100                 105                 110

Val Ser Ser
        115
```

<210> SEQ ID NO 10
<211> LENGTH: 113
<212> TYPE: PRT
<213> ORGANISM: Artificial Sequence

```
<220> FEATURE:
<223> OTHER INFORMATION: Description of Artificial Sequence: Synthetic
      consensus sequence
<220> FEATURE:
<221> NAME/KEY: MOD_RES
<222> LOCATION: (3)..(3)
<223> OTHER INFORMATION: Leu or Val
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (10)..(10)
<223> OTHER INFORMATION: Thr or Ser
<220> FEATURE:
<221> NAME/KEY: MOD_RES
<222> LOCATION: (12)..(12)
<223> OTHER INFORMATION: Ser or Pro
<220> FEATURE:
<221> NAME/KEY: MOD_RES
<222> LOCATION: (15)..(15)
<223> OTHER INFORMATION: Ile or Leu
<220> FEATURE:
<221> NAME/KEY: MOD_RES
<222> LOCATION: (24)..(24)
<223> OTHER INFORMATION: Lys or Arg
<220> FEATURE:
<221> NAME/KEY: MOD_RES
<222> LOCATION: (30)..(30)
<223> OTHER INFORMATION: Ile or Val
<220> FEATURE:
<221> NAME/KEY: MOD_RES
<222> LOCATION: (31)..(31)
<223> OTHER INFORMATION: Asp or Tyr
<220> FEATURE:
<221> NAME/KEY: MOD_RES
<222> LOCATION: (35)..(35)
<223> OTHER INFORMATION: Lys or Asn
<220> FEATURE:
<221> NAME/KEY: MOD_RES
<222> LOCATION: (37)..(37)
<223> OTHER INFORMATION: Phe or Tyr
<220> FEATURE:
<221> NAME/KEY: MOD_RES
<222> LOCATION: (41)..(41)
<223> OTHER INFORMATION: Leu or Phe
<220> FEATURE:
<221> NAME/KEY: MOD_RES
<222> LOCATION: (42)..(42)
<223> OTHER INFORMATION: Leu or Gln
<220> FEATURE:
<221> NAME/KEY: MOD_RES
<222> LOCATION: (50)..(50)
<223> OTHER INFORMATION: Lys or Arg
<220> FEATURE:
<221> NAME/KEY: MOD_RES
<222> LOCATION: (55)..(55)
<223> OTHER INFORMATION: Leu or Lys
<220> FEATURE:
<221> NAME/KEY: MOD_RES
<222> LOCATION: (58)..(58)
<223> OTHER INFORMATION: Lys or Asn
<220> FEATURE:
<221> NAME/KEY: MOD_RES
<222> LOCATION: (59)..(59)
<223> OTHER INFORMATION: Leu or Trp
<220> FEATURE:
<221> NAME/KEY: MOD_RES
<222> LOCATION: (68)..(68)
<223> OTHER INFORMATION: Thr or Ser
<220> FEATURE:
<221> NAME/KEY: MOD_RES
<222> LOCATION: (88)..(88)
<223> OTHER INFORMATION: Leu or Val
<220> FEATURE:
<221> NAME/KEY: MOD_RES
<222> LOCATION: (90)..(90)
<223> OTHER INFORMATION: Leu or Val
```

```
<220> FEATURE:
<221> NAME/KEY: MOD_RES
<222> LOCATION: (94)..(94)
<223> OTHER INFORMATION: Trp or Met
<220> FEATURE:
<221> NAME/KEY: MOD_RES
<222> LOCATION: (99)..(99)
<223> OTHER INFORMATION: Phe or Trp
<220> FEATURE:
<221> NAME/KEY: MOD_RES
<222> LOCATION: (101)..(101)
<223> OTHER INFORMATION: May or may not be present
<220> FEATURE:
<221> NAME/KEY: MOD_RES
<222> LOCATION: (105)..(105)
<223> OTHER INFORMATION: Gly or Gln
<220> FEATURE:
<221> NAME/KEY: MOD_RES
<222> LOCATION: (113)..(113)
<223> OTHER INFORMATION: May or may not be present

<400> SEQUENCE: 10

Asp Val Xaa Met Thr Gln Xaa Pro Leu Xaa Leu Xaa Val Thr Xaa Gly
1               5                   10                  15

Gln Pro Ala Ser Ile Ser Cys Xaa Ser Ser Gln Ser Leu Xaa Xaa Ser
            20                  25                  30

Asp Gly Xaa Thr Xaa Leu Asn Trp Xaa Xaa Gln Arg Pro Gly Gln Ser
        35              40                  45

Pro Xaa Arg Leu Ile Tyr Xaa Val Ser Xaa Xaa Asp Ser Gly Val Pro
    50                  55                  60

Asp Arg Phe Xaa Gly Ser Gly Ser Gly Thr Asp Phe Thr Leu Lys Ile
65              70                  75                  80

Ser Arg Val Glu Ala Glu Asp Xaa Gly Xaa Tyr Tyr Cys Xaa Gln Gly
                85                  90                  95

Thr His Xaa Pro Tyr Thr Phe Gly Xaa Gly Thr Lys Leu Glu Ile Lys
            100                 105                 110

Arg

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asn Tyr Trp Met His
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Tyr Tyr Gly Tyr Asp
1               5

<210> SEQ ID NO 13
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 13

Lys Ser Ser Gln Ser Leu Ile Asp Ser Asp Gly Lys Thr Phe Leu Asn
1               5                   10                  15

Trp

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Val Ser Lys Leu Asp Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Trp Gln Gly Thr His Phe Pro Tyr Thr
1               5
```

METHODS FOR TREATING GI SYNDROME AND GRAFT VERSUS HOST DISEASE

CROSS-REFERENCE TO RELATED APPLICATION

This application is a National Stage of PCT Application No. PCT/US2013/042941, filed on May 28, 2013, which itself claims benefit of Provisional Application Ser. No. 61/651,729, filed May 25, 2012, the entire contents of which are hereby incorporated by reference as if fully set forth herein, under 35 U.S.C. § 119(e).

STATEMENT OF GOVERNMENTAL INTEREST

This invention was made with government support under CA085704 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on May 25, 2017, is named 115872-1306_SL.txt and is 21,238 bytes in size.

BACKGROUND

Radiation remains one of the most effective treatments for a wide variety of malignant cells; however, healthy cells of the bone marrow, hair follicle, epidermis and gastrointestinal tract are extremely sensitive to radiation cell death, limiting the effective use of this therapy for the treatment of cancer. Radiation gastrointestinal (GI) syndrome is a typical consequence of radiation disease and it is a major lethal toxicity that may occur after a radiation/nuclear incident. The possibility of a radiologic disaster by way of nuclear detonation or accident has long existed, however the threat of attack with a radiation dispersal device has increased the urgency for safe and effective medical radiation countermeasures (MRCs). The Project BioShield Act and Department of Health and Human Services estimate that an effective MRC mitigator must be effective even when administered 24 h after a nuclear disaster, as this represents the minimum time necessary to mobilize treatment to a significant portion of an urban population. The Radiation Gastrointestinal (GI) Syndrome (RGS) is a major lethal toxicity that involves destruction of the intestinal stem cell compartment within crypt/villus units, resulting in mucosal denudation, loss of nutrient adsorption and susceptibility to infection by resident bacterial flora. Clinically, RGS presents with anorexia, vomiting, diarrhea, dehydration, systemic infection, and in extreme cases, septic shock and death. Despite extensive study of the effects of radiation on normal tissue, no effective prophylactic or therapeutic mitigator of the Radiation GI Syndrome are available for first responders, military personnel, or remediation workers entering a contaminated area.

Hematopoietic stem cell transplantation (including bone marrow transplants, peripheral blood stem cell donations, and stem cells from umbilical cord blood) is another way to treat advanced cancer; however, tissue transplants frequently evoke a variety of immune responses in the host, which results in rejection of the graft and graft versus host disease ("GvHD"). GvHD is a type of T-cell-mediated autoimmune disease. Hematopoietic stem cell transplants, especially bone marrow transplants are currently used to treat a number of malignant and non-malignant diseases including acute and chronic leukemias, myelomas, solid tumors (R. J. Jones, Curr Opin Oncol 3 (2), 234 (1991); G. L. Phillips, Prog Clin Biol Res 354B, 171 (1990)), aplastic anemias and severe immunodeficiencies (R. P. Gale, R. E. Champlin, S. A. Feig et al., Ann Intern Med 95 (4), 477 (1981); G. M. Silber, J. A. Winkelstein, R. C. Moen et al., Clin Immunol Immunopathol 44 (3), 317 (1987)). The conditioning regimen required prior to transplantation, designed to ablate or suppress the patient's immune system, renders the patient susceptible to neoplastic relapse or infection.

Recent use of unrelated and HLA non-identical donors has unfortunately increased the incidence of GvHD. While removal of T-cells from the donor marrow graft ameliorates GvHD, this strategy increases graft failure rates and markedly diminishes the therapeutically-beneficial graft-versus-tumor effect. As such, overall survival does not improve. Further, despite strong pre-clinical data, attempts to improve GvHD outcomes by diminishing inflammatory cytokine action by adding TNF antagonists to corticosteroids, the standard of care for acute GvHD, has provided limited therapeutic benefit.

Thus, there is an urgent need for alternative strategies to reduce the incidence and severity of radiation disease, GI syndrome, GvHD and other autoimmune diseases where GI damage leads to morbidity/mortality from sepsis in an animal as well as conditions characterized by high levels of endothelial apoptosis.

SUMMARY OF THE INVENTION

Applicants have determined that the prior techniques suffer from one or more deficiencies, including the scarcity of efficient means of preventing and treating diseases in animals such as GI syndrome, GvHD, radiation disease and certain autoimmune diseases associated with GI damage, as well as conditions characterized by high levels of endothelial apoptosis and diseases associated with the formation of ceramide-rich platforms (CRP) (hereinafter the "enumerated diseases"). Although most of the methods will be used to treat (including "mitigate") an enumerated disease, if the treatment is administered early enough, for example before irradiation of the subject or before the subject receives a graft, then the corresponding disease (GI syndrome or GvHD, respectively), may be prevented.

In a first set of embodiments, methods are provided for preventing or treating an enumerated disease in an animal by administering a prophylactically or therapeutically effective amount of at least one antibiotic that targets Gram-negative bacteria together with an anti-ceramide antibody, or a biologically active fragment thereof. Antibiotics for use in the embodiments include broad spectrum antimicrobials that cover both Gram-positive and Gram-negative organisms, including quinolones (Baytril, ciprofloxacin), cephalosporins (cefepime, ceftazidine) or aminoglycosides (gentamicin, amikacin) together with a therapeutically effective amount of any anti-ceramide antibody. Anti-ceramide antibodies include but are not limited to a humanized anti-ceramide antibodies such as h2A2, or fully human anti-ceramide antibodies. Other antibodies that are useful in embodiments of the invention include anti-ceramide monoclonal (e.g., 1H4, 15D9, 5H9, and 2A2 and humanized versions thereof, and h2A2, and 2A2 polyclonal, or genetically-engineered antibodies, or a biologically active fragment or variant thereof. The monoclonal antibodies, in certain embodiments, can cross-react with ceramide. The mouse 2A2 antibody has been deposited with the ATCC. It has the Identification Reference by Depositor of *Myeloma cell fused with spleen cells from Balb/c mouse*: 2A2.1.1.1.1. and the ATCC® Patent Deposit Designation PTA-13418.

Prophylactically and therapeutically effective amounts of the anti-ceramide antibody are from about 0.1 mg/kg to about 100 mg/kg and from about 100 mg/kg to about 1000 mg/kg. Prophylactically and therapeutically effective amounts of the one or more antibiotics that are administered with the anti-ceramide antibody vary widely depending on the antibiotic, the formulation, the route of administration, etc. but can also range from about 0.1 mg/kg to about 100 mg/kg, about 100 mg/kg to about 1000 mg/kg. The antibiotic and the antibody can be administered simultaneously, for example in a single pharmaceutical formulation, or sequentially. "Therapeutic agents" herein refers to the anti-ceramide antibodies and mimotopes and the antibiotics targeting gram negative bacteria.

Quinolone antibiotics for use in various embodiments are selected from the group including Enrofloxacin (i.e., Baytril), Ciprofloxacin (i.e., Cipro and Proquin), Enoxacin (i.e., Penetrex), Gatifloxacin i.e., Gatiflo, Tequin and Zymar), Gemifloxacin (i.e., Factive), Levofloxacin (i.e., Levaquin), Lomefloxacin (i.e., Maxaquin), Moxifloxacin (i.e., Avelox), Norfloxacin (i.e., Noroxin), Ofloxacin (i.e., Floxin), Prulifloxacin, Sparfloxacin (i.e., Zagam), Trovafloxacin/Altrofloxacin (i.e., Trovan), Danofloxacin (i.e., A180), Difloxacin (i.e., Dicural), Marbofloxacin Orbax), Orbifloxacin (i.e., Zeniquin), Naldixic acid (i.e., NegGram), Cinoxacin (i.e., Cinobac), Flumequine, Nalidixic acid, Oxolinic acid, Pipemidic acid, Piromidic acid, Rosoxacin, Fleroxacin, Pefloxacin, Rufloxacin, Balofloxacin, Grepafloxacin, Pazufloxacin, Temafloxacin, Tosufloxacin, Besifloxacin, Clinafloxacin, Garenoxacin, Sitafloxacin, Ibafloxacin, Pradofloxacin, and Sarafloxacin.

In addition to or instead of antibodies, mimotopes of one or more the ceramide epitopes or chemical compounds with essentially the same binding as mimotopes (i.e. derived from chemical backbone library screening) can be administered in therapeutically effective amounts.

To mitigate one or more of the enumerated diseases, the therapeutic agents are administered before symptoms of the disease are manifest (such as in the case of GvHD and certain defined autoimmune diseases), or after radiation exposure (as in the case of radiation disease or GI syndrome. In mitigating certain enumerated diseases, the therapeutic agents are administered before or after irradiation or before or after receipt of a graft, e.g., a hematopoietic stem cell transplant. Although most of the methods will be used to treat (including "mitigate") an enumerated disease, if the treatment is administered early enough, for example before irradiation of the subject or before the subject receives a graft, then the corresponding disease (GI syndrome or GvHD, respectively), may be prevented.

In a second set of embodiments, a pharmaceutical composition is provided that is useful for preventing or treating one of the enumerated diseases in an animal, comprising prophylactically or therapeutically effective amounts of an anti-ceramide antibody such as h2A2, including a monoclonal antibody such as 1H4, 15D9, 5H9, and 2A2 and humanized versions thereof, and h2A2 and 2A2 IgM, a polyclonal, genetically-engineered or a fully human antibody, or a biologically active fragment or variant thereof or a statin, or imipramine, and one or more of the enumerated antibiotics described herein that treat or prevent gram negative bacterial infections, including broad-based antibiotics, in a pharmaceutically acceptable carrier.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

Figure 1:
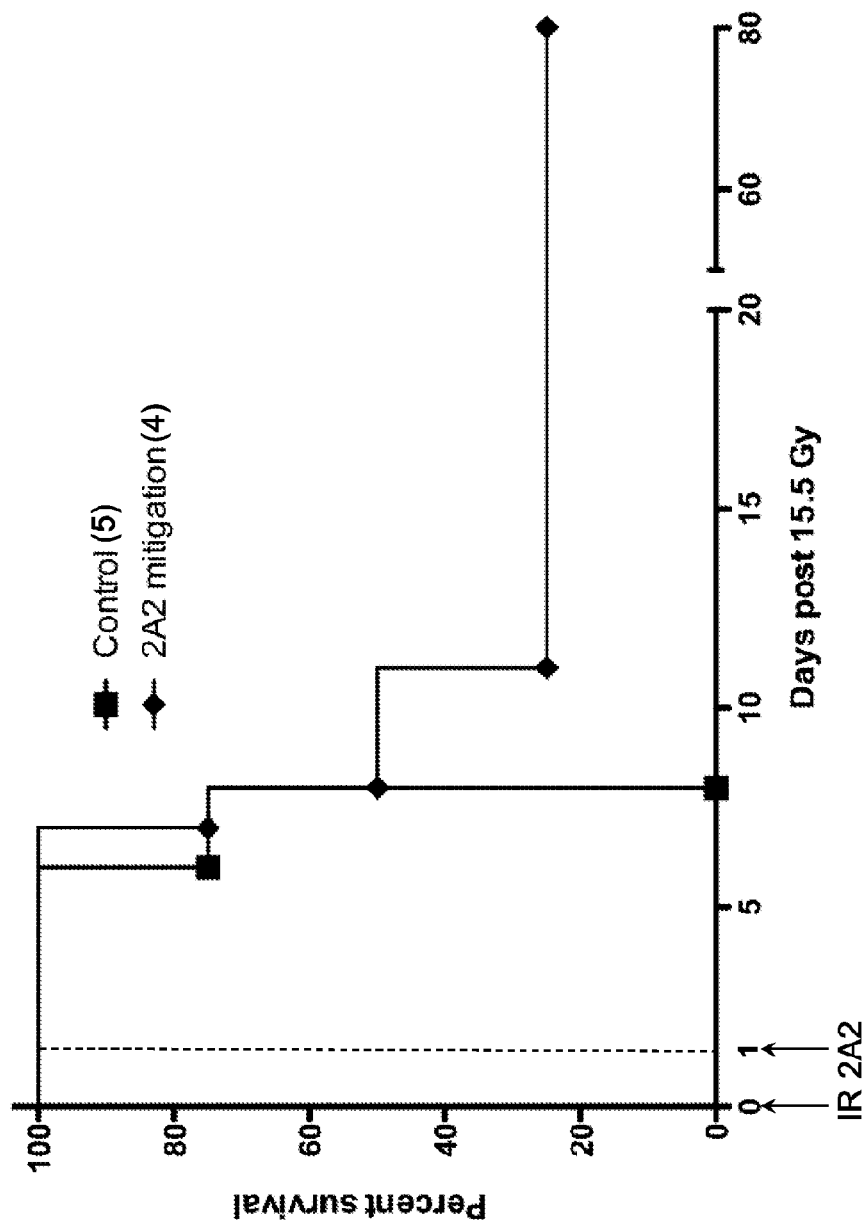
FIG. 1. Purified monoclonal 2A2 Ab administered 24 hours following 15.5 Gy subtotal body irradiation (SBI) improves mouse survival.

It has now been discovered that administering an anti-ceramide antibody together with an antibiotic that targets Gram-negative bacteria results in unexpected synergy in preventing, mitigating and treating GvHD, radiation disease, GI syndrome, those autoimmune diseases where GI damage leads to morbidity/mortality from sepsis in an animal, and other diseases that are associated with CRP production (the "enumerated diseases"), including diseases mediated by cytolytic T lymphocyte (CTL)-induced killing and/or by damage to endothelial microvasculature. The antibody can be a monoclonal, polyclonal, genetically-engineered, humanized or a fully human antibody, or a biologically active fragment or variant thereof such as an Fv fragment or single domain antibodies. In addition to or instead of antibodies, mimotopes that bind to ceramide or chemical compounds with essentially the same binding as mimotopes can be administered in therapeutically effective amounts. Therefore certain embodiments are directed to methods of treating, mitigating or preventing an enumerated disease by administering therapeutic or prophylactic amounts of an anti-ceramide antibody, or biologically active fragment or variant thereof, or mimotope, together with prophylactically or therapeutically effective amounts of an antibiotic that targets Gram-negative bacteria. The useful antibiotics include broad spectrum antimicrobials that cover both Gram-positive and Gram-negative organisms, such as quinolones (Baytril, ciprofloxacin), cephalosporins (cefepime, ceftazidine) and aminoglycosides (gentamicin, amikacin). The antibody and antibiotic and mimotopes (herein "the therapeutic agents") can be administered before or after irradiation or a tissue transplant, or upon diagnosis of GI syndrome, GvHD, an autoimmune disease involving damage to the gut or other disease associated with CRP formation. The therapeutic agents can be administered simultaneously, or at different times and via different routes.

Other embodiments are directed to pharmaceutical compositions that can be administered to prevent or treat an enumerated disease, comprising prophylactic or therapeutic amounts of an anti-ceramide antibody, or biologically active fragment or variant thereof, or ceramide-binding mimotopes together with an antibiotic that targets Gram-negative bacteria, including broad spectrum antibiotics.

In the following description, for the purposes of explanation, numerous specific details are set forth in order to provide a thorough understanding of the present invention. It will be apparent, however, to one skilled in the art that the present invention may be practiced without these specific details.

The invention is described with reference to specific embodiments. It will, however, be evident that various modifications and changes may be made thereto without departing from the broader spirit and scope of the invention. The specification and drawings are, accordingly, to be regarded in an illustrative rather than a restrictive sense. The invention is illustrated herein by the experiments described above and by the following examples, which should not be construed as limiting. The contents of all references, pending patent applications and published patents, cited throughout this application are hereby expressly incorporated by reference. Although specific terms are employed, they are used as in the art unless otherwise indicated.

The following terms as used herein have the corresponding meanings given here.

1. Definitions

Generally, nomenclatures used in connection with, and techniques of, cell and tissue culture, molecular biology, immunology, microbiology, genetics, protein, and nucleic acid, chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. See, e.g., Sambrook et al., Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Principles of Neural Science, 4th ed., Eric R. Kandel, James H. Schwan, Thomas M. Jessell editors. McGraw-Hill/Appleton & Lange: New York, N.Y. (2000). Unless defined otherwise, all technical and scientific terms used herein have the same meaning as commonly understood by one of ordinary skill in the art.

"Antibiotics for use in the present invention" as used herein, mean any antibiotics that are effective against Gram-negative bacteria, including broad spectrum antimicrobials that cover both Gram-positive and Gram-negative organisms. These include quinolones (Baytril, ciprofloxacin), cephalosporins (cefepime, ceftazidine) or aminoglycosides (gentamicin, amikacin). In recent experiments, it was shown that Baytril improved survival from the GI syndrome, while sulfatrim (sulfonamide and trimethoprim) had no effect. This indicates that broad spectrum antimicrobials that cover Gram-negative organisms may be more effective than antibiotics that specifically target Gram-negative bacteria.

"Autoimmune diseases" that come within the scope of the enumerated diseases as used herein, mean, but are not limited to GvHD and those autoimmune diseases accompanied by GI damage "Effective amount" as used herein, means an amount of a therapeutic agent, which produces a desired effect.

"Enumerated disease" as used herein, means any disease that can be treated (including mitigated) or prevented by administering treatment according to an embodiment of the invention. Enumerated diseases include Radiation disease, GvHD, GI syndrome and an autoimmune disease associated with GI damage, or diseases and conditions characterized by high levels of endothelial apoptosis including, rheumatoid arthritis and multiple sclerosis. Also included are diseases associated with CRP formation and diseases mediated by cytolytic T lymphocyte (CTL)-induced killing and/or by damage to endothelial microvasculature.

"Gastrointestinal (GI) syndrome" as used herein means the full syndrome will usually occur with a dose greater than approximately 10 Gy (1000 rads) although some symptoms may occur as low as 6 Gy or 600 rads.

"Mimotope" as used herein, means a macromolecule, often a peptide, which mimics the structure of an epitope. Because of this property it causes an antibody response similar to the one elicited by the epitope. An antibody for a given epitope antigen will recognize a mimotope which mimics that epitope. Mimotopes are commonly obtained from phage display libraries through biopanning. Mimotoptes are useful in initiating an immune response in the subject causing him/her to generate endogenous anti-ceramide antibodies that would treat the enumerated disease.

"Mitigating a disease" as used herein, means reducing or ameliorating a disease or symptom of a disease. For example, radiation disease can be mitigated by administering a therapeutic agent after exposure but prior to phenotypic expression of the disease (i.e. prior to the appearance of symptoms of the disease). Mitigation includes making the effects of disease less severe by avoiding, containing, reducing or removing it or a symptom of it. Mitigating an enumerated disease as described herein comes within the definition of "treating" an enumerated disease before symptoms occur. Amounts of therapeutic agents that mitigate a disease are herein referred to as "therapeutically effective amounts."

"Prophylactically effective amount" as used herein, means an amount of a therapeutic agent, which, when administered to a subject, will have the intended prophylactic effect e.g., preventing or delaying the onset (or reoccurrence) of a disease or set of one or more symptoms, or reducing the likelihood of the onset (or reoccurrence) of the disease or set of symptoms. The full prophylactic effect does not necessarily occur by administration of one dose and may occur only after administration of a series of doses. Thus, a prophylactically effective amount may be administered in one or more administrations.

"Prophylactic, Mitigating and Therapeutic Agents" as used herein means any anti-ceramide antibody and also broad spectrum antimicrobials that cover Gram-negative organisms, such as quinolones (Baytril, ciprofloxacin), cephalosporins (cefepime, ceftazidine) or aminoglycosides (gentamicin, amikacin).

"Subject" as used herein, means an organism that is an object of a method or material, including mammals, e.g., humans, dogs, cows, horses, kangaroos, pigs, sheep, goats, cats, mice, rabbits, rats, and transgenic non-human animals. Synonyms used herein include "patient" and "animal."

"Therapeutically effective amount" as used herein means an amount of a therapeutic agent that achieves an intended therapeutic effect in a subject, e.g., eliminating or reducing or mitigating the severity of a disease or set of one or more symptoms. The full therapeutic effect does not necessarily occur by administration of one dose and may occur only after administration of a series of doses. Thus, a therapeutically effective amount may be administered in one or more administrations.

"Treating" as used herein means taking steps to obtain beneficial or desired results, including clinical results, including mitigating, alleviating or ameliorating one or more symptoms of a disease; diminishing the extent of disease; delaying or slowing disease progression; ameliorating and palliating or stabilizing a metric (statistic) of disease. The effect may be prophylactic in terms of completely or partially preventing a conditions or disease or symptom thereof and/or may be therapeutic in terms of a partial or complete cure for a condition or disease and/or adverse effect attributable to the condition or disease. "Treatment" refers to the steps taken. It can include any treatment of a condition or disease in a mammal, particularly in a human, and includes: (a) preventing the condition or disease or symptom thereof from occurring in a subject which may be predisposed to the condition or disease but has not yet been diagnosed as having it; (b) inhibiting the condition or disease or symptom thereof, such as, arresting its development; and (c) relieving, alleviating or ameliorating the condition or disease or symptom thereof, such as, for example causing regression of the condition or disease or symptom thereof.

2. Overview

Extracellular Cell Surface Ceramide is Required for Radiation Apoptosis

It has long been accepted that the clonogenic compartment of the gastrointestinal (GI) mucosa is the specific and direct target for radiation-induced GI damage. Characterized clinically by anorexia, vomiting, diarrhea, dehydration, systemic infection, and, in extreme cases, septic shock and death, the radiation gastrointestinal (GI) syndrome involves destruction of crypthillus units, loss of mucosal integrity, and infection by resident enterobacterial flora (See Hendry, J. H., Potten C. S., Roberts N. P. The gastrointestinal syndrome and mucosal clonogenic cells: relationships between target cell sensitivities, LD50 and cell survival, and their modification by antibiotics. *Radiat Res.* 1983; 96 (1): 100-112; Hendry, J. H., Roberts S. A., Potten C. S. The clonogen content of murine intestinal crypts: dependence on radiation dose used in its determination. *Radiat Res.* 1992; 132 (1): 115-119; Potten C. S., A comprehensive study of the radiobiological response of the murine (BDF1) small intestine. *Int. J. Radiat Biol.* 1990; 58 (6): 925-973.)). While conventional radiobiology considers unrepaired or misrepaired DNA double strand breaks in stem cell clonogens (SCCs) as autonomous lesions leading to irreversible tissue injury, our recent studies have challenged this paradigm, presenting genetic evidence that acute endothelial damage also plays a major role in GI tract injury (Paris F., et al., Endothelial apoptosis as the primary lesion initiating intestinal radiation damage in mice. Science. 2001; 293 (5528): 293-297; Rotolo J. A., Kolesnick R., Fuks Z. Timing of lethality from gastrointestinal syndrome in mice revisited. *Int J Radial Oncol Biol Phys.* 2009; 73 (1): 6-8; Rotolo J. A., et al., Bax and Bak do not exhibit functional redundancy in mediating radiation-induced endothelial apoptosis in the intestinal mucosa. *Int J Radiat Oncol Biol Phys.* 2008; 70 (3): 804-815). Within minutes of radiation exposure, endothelial acid sphingomyelinase (ASMase) is activated, catalyzing ceramide generation on the external plasma membrane of mouse and human endothelium to initiate apoptotic signaling (Stancevic B., Kolesnick R., Ceramide-rich platforms in transmembrane signaling. *FEBS Lett.* 2010; 584

(9): 1728-1740; Truman J. P., et al. Endothelial membrane remodeling is obligate for anti-angiogenic radio sensitization during tumor radiosurgery. *PLoS One.* 2010; 5 (9)). Endothelium displays 20-fold more ASMase than other mammalian cells, almost exclusively in a secretory form, which makes them particularly vulnerable to ceramide-induced apoptosis (Marathe S., et al. Human vascular endothelial cells are a rich and regulatable source of secretory sphingomyelinase. Implications for early atherogenesis and ceramide-mediated cell signaling. *J. Biol. Chem.* 1998; 273 (7): 4081-4088; Santana P., et al., Acid sphingomyelinase-deficient human lymphoblasts and mice are defective in radiation-induced apoptosis. *Cell.* 1996; 86 (2): 189-199.) Early evidence indicates that vascular compromise, consequent to endothelial cell apoptosis, impairs radiation-injured SCC DNA damage repair, resulting in SCC demise. In several mouse strains, endothelial apoptosis occurs between 8 and 15 Gy, which encompasses doses that cause both sublethal ($\leq$14 Gy) and lethal ($\geq$15 Gy) GI tract injury (5), beginning at 1 hour and peaking at 4 to 6 hours after irradiation (Maj J. G., Paris F., Haimovitz-Friedman A, Venkatraman E., Kolesnick R., Fuks, Z. Microvascular function regulates intestinal crypt response to radiation. *Cancer Res.* 2003; 63 (15): 4338-4341.) Attenuation of intestinal endothelial apoptosis by genetic inactivation of ASMase-mediated ceramide generation enhances SCC survival, facilitating repair of crypt damage and rescue of animals from GI lethality (Paris, F., et al. Endothelial apoptosis as the primary lesion initiating intestinal radiation damage in mice. *Science.* 2001; 293 (5528): 293-297); Rotolo, J. A., et al. Bax and Bak do not exhibit functional redundancy in mediating radiation-induced endothelial apoptosis in the intestinal mucosa. *Int J Radiat Oncol Biol Phys.* 2008; 70 (3): 804-815.) These observations provide the basis for developing a neutralizing anti-ceramide monoclonal antibody as a potential radiation countermeasure. Radiation targets both the gastrointestinal microvasculature and proliferating crypt stem cells. Apoptosis of the microvascular endothelium in the villus is an important lesion of the GI syndrome, occurring about 4 hours following radiation. Endothelial apoptosis converts lesions to the crypt clonogens from sublethal to lethal, resulting in loss of regenerative crypts and promoting GI toxicity. It has also been discovered that the endothelial injury couples to repair of DNA damage in the stem cell compartment making GI lethality a synthetic event resulting from direct damage to stem cell clonogens coupled to vascular dysfunction.

Pathophysiology of GI syndrome, also called Radiation Gastrointestinal (GI) Syndrome (RGS) requires depletion of stem cell clonogens (SCCs) within the Crypts of Lieberkühn, necessary for post-injury regeneration of gut epithelium. However, SCC reproductive death is not exclusively a result of DNA damage, but is critically coupled to ceramide-induced endothelial cell apoptosis within the mucosal microvascular network. Ceramide generated on the surface of endothelium coalesces to form ceramide-rich platforms (CRPs) that transmit an apoptotic signal (Stancevic B., Kolesnick R. Ceramide-rich platforms in transmembrane signaling. *FEBS Lett.* 2010; 584 (9): 1728-1740; Haimovitz-Friedman A., et al. Ionizing radiation acts on cellular membranes to generate ceramide and initiate apoptosis. *J Exp Med.* 1994; 180 (2): 525-535; Verheij M., et al. Requirement for ceramide-initiated SAPK/JNK signaling in stress-induced apoptosis. *Nature.* 1996; 380 (6569): 75-79; Liao W. C., et al. Ataxia telangiectasia-mutated gene product inhibits DNA damage-induced apoptosis via ceramide synthase. *J Biol Chem.* 1999: 274 (25): 17908-17917). We have shown that CRPs are amenable to pharmacologic inactivation, specifically pharmacologic inhibition of CRP formation with an antibody to ceramide attenuated endothelial damage, enhanced crypt stem cell clonogen survival, and thereby increased tissue regeneration, even following lethal radiation doses. See Rotolo, et al., Anti-ceramide antibody prevents the radiation gastrointestinal syndrome in mice, *J Clin Invest.* 2012; 122(5):1786-1790, and Rotolo, et al., U.S. patent application Ser. No. 12/599,280.

In initial studies ionizing radiation (10 Gy) induced a rapid increase in BAEC ASMase enzymatic activity while concomitantly increasing cellular ceramide within 1 minute of stimulation. Simultaneous increase of neutral sphingomyelinase or ceramide synthase activity was not detected, confirming that radiation-induced ceramide generation was ASMase-mediated. Formation of ceramide-rich platforms (CRPs) was detected as early as 30 seconds after irradiation, and was dose dependent at 1 minute, reaching a maximum at 11 Gy (P<0.001), with an ED50 of approximately 5 Gy. Preincubation of BAECs with MID 15B4 (a commercially available anti-ceramide antibody), a strategy known to neutralize cell surface ceramide and block ceramide-induced coalescence in other cell types (Rotolo J. A., Zhang J., Donepudi M., Lee H., Fuks Z., Kolesnick R. Caspase-dependent and -independent activation of acid sphingomyelinase signaling. *J Biol Chem.* 2005; 280 (28): 26425-26434; Grassmé H., et al. CD95 signaling via ceramide-rich membrane rafts. *J Biol Chem.* 2001; 276 (23): 20589-20596; Grassmé H., et al. Host defense against *Pseudomonas aeruginosa* requires ceramide-rich membrane rafts. *Nat Med.* 2003; 9 (3): 322-330; Göggel R., et al. PAF-mediated pulmonary edema: a new role for acid sphingomyelinase and ceramide. *Nat Med.* 2004; 10 (2): 155-160), inhibited radiation-induced formation of CRPs at a dose range that is virtually identical to that published for induction of radiation-induced apoptosis in BAECs (Fuks Z., et al. Basic fibroblast growth factor protects endothelial cells against radiation-induced programmed cell death in vitro and in vivo. *Cancer Res.* 1994; 54 (10): 2582-2590.) Surface ceramide neutralization and CRP inhibition attenuated 10 Gy-induced apoptosis by 71% for up to 8 hours after stimulation.

We also reported similar anti-ceramide antibody inhibition of radiation-induced (5-20 Gy) CRP formation and apoptosis in Jurkat T lymphocytes where pre-incubation of Jurkat T cells with anti-ceramide MID15B4 (1 microgram/nil) 15 min prior to 10 Gy IR attenuated platform generation. It was also shown that sequestration of ceramide protected C57BL/6 intestinal mucosa against radiation-induced microvascular endothelial apoptosis, crypt stem cell death and lethal GI toxicity. U.S. patent application Ser. No. 12/599, 280.

Our mouse monoclonal anti-ceramide IgM, termed 2A2, has specific affinity for ceramide. 2A2 inhibits CRP formation and ceramide-mediated apoptosis and dose dependently inhibited endothelial cell apoptosis in vivo. Intravenous 2A2 administration (1,000 μg/25 g mouse) to C57BL/6 mice 15 minutes prior to the LD100 of 15 Gy whole-body irradiation (WBI) reduced peak endothelial apoptosis within the lamina propria microvasculature by 83%. Thus, 2A2 phenocopies the genetic inhibition of radiation-induced intestinal endothelial apoptosis conferred by ASMase deletion in ASMase−/− mice, As little as 50 μg 2A2 antibody/25 g mouse increased the number of surviving crypts (P<0.05), while maximal protection was achieved with 1,000 μg 2A2 antibody/25 g mouse which is 40 mg/kg. 2A2 administration was without toxicity. 100% of animals receiving 2A2 were saved from radiation GI syndrome lethality at 15 Gy total body irradiation. In contrast, 100% of animals receiving irrelevant IgM (isotype control) or no antibody (vehicle only) consistently died with denuded intestinal mucosa and clinical evidence of radiation GI syndrome lethality. At the LD50 dose of 14 Gy total body irradiation, 2A2 plus hematopoietic stem cell transplant (HSCT) saved 100% of irradiated animals. Even at the very high radiation dose of 17 Gy total body irradiation, 2A2 protected 50% of GI tracts, as 25% of the 2A2-pretreated mice survived ad infinitum, and 33% of those that succumbed died with intact GI tracts. Further studies showed that HSCT did not contribute to the protective effects of 2A2.

Thus, 2A2 monoclonal antibody is prototype of a new class of anti-ceramide therapeutics (Rotolo J. A., Kolesnick R., Pasqualini R., Arap W., inventors: Sloan Kettering Institute For Cancer research, assignee. Methods for treating and preventing GI syndrome and graft versus host disease. U.S. patent application Ser. No. 12/599,280. May 6, 2008), that can be used as an effective countermeasure against the lethal radiation GI syndrome.

Recently we identified a new humanized 2A2 antibody that has even higher binding affinity for ceramide than the original mouse 2A2 antibody. Details of making this antibody and its sequence are set forth in the Examples below.

3. Background

Ceramide Signaling is Important Across Many Species

Ceramide-mediated raft clustering is a site of signal transduction for bacteria and pathogen internalization. (D. A. Brown and E. London, *Annu Rev Cell Dev Biol* 14, 111 (1998); J. C. Fanzo, M. P. Lynch, H. Phee et al., *Cancer Biol Ther* 2 (4), 392 (2003); S. Lacour, A. Hammann, S. Grazide et al., *Cancer Res* 64 (10), 3593 (2004); Semac, C. Palomba, K. Kulangara et al., *Cancer Res* 63 (2), 534 (2003); A. B. Abdel Shakor, K. Kwiatkowska, and A. Sobota, *J Biol Chem* 279 (35), 36778 (2004); H. Grassme, V. Jendrossek, J. Bock et al., *J Immunol* 168 (1), 298 (2002); M. S. Cragg, S. M. Morgan, H. T. Chan et al., *Blood* 101 (3), 1045 (2003); D. Scheel-Toellner, K. Wang, L. K. Assi et al., *Biochem Soc Trans* 32 (Pt 5), 679 (2004); D. Delmas, C. Rebe, S. Lacour et al., *J Biol Chem* 278 (42), 41482 (2003); and C. Bezombes, S. Grazide, C. Garret et al., *Blood* 104 (4), 1166 (2004)). The unique biophysical properties of ceramide render it proficient in formation of signaling domains termed ceramide-rich platforms (CRPs) that possess a general function in signal transduction for a variety of stimuli. This theory is also supported by the fact that CRPs are formed in response to a variety of somewhat unrelated cellular stimuli (see Table 1).

TABLE 1

Ceramide-rich platform formation in biological systems.

| Stimulus | Cell type | Cellular outcome | Reference |
|---|---|---|---|
| FasL, CH 11 | Jurkat T lymphocytes JY B Cell Lymphocytes H9 (Human T Cells) SKW 6.4 Cells (Human B Lymphocytes) K50 Cells (Burkitt Lymphoma Cells) WI 38 Cells (Human Lung Fibroblasts) H9 T Cell Lymphoma Human PBL* Murine Granulosa Cells* Lung Epithelial Cells Murine and Human Lymphocytes* Murine Splenocytes and Hepatocytes* Coronary Artery Endothelial Cells* | Apoptosis | [57, 59, 94, 99, 122-125] |
| TNFα | Coronary Artery Endothelial Cells* | Apoptosis | [123] |
| Endostatin | Coronary Artery Endothelial Cells* | Apoptosis | [123, 126] |
| CD40L | JY B Lymphocytes Human Aortic Endothelial Cells* | Activation | [60, 106] [127] |
| Rituximab (CD20) | Daudi Cells (Burkitt Lymphoma) RL Cells (Follicular lymphoma) Chronic Lymphocyte Leukemia (CLL) Cells* | Growth inhibition | [86] |
| TRAIL | Murine T Splenocytes* BJAB Cells (Burkitt Lymphoma) A549 (Carcinomic Human Alveolar Basal Epithelial Cells) L929 Cells (Murine Aneuploid Fibrosarcoma) | Apoptosis | [61] |
| UV-C | U937 Cells (Human Myeloblastoma) Jurkat T Lymphocytes | Apoptosis | [69, 70] |
| γ-irradiation | Jurkat T Lymphocytes Bovine Aortic Endothelial Cells* SCC61 Cells (Head and Neck Squamous Carcinoma) | Apoptosis | (Zhang and Kolesnick, unpublished) (Stancevic and Kolesnick, unpublished) [98] |
| *P. aureginosa* | Human Nasal Epithelial Cells* Chang Conjunctive Epithelial Cells Murine Tracheal Epithelial Cells (in vivo) Murine Lung Fibroblasts* WI-38 Cells (Human Lung Fibroblasts) Alveolar Macrophages* | Apoptosis Internalization IL-12 release | [82, 128] |
| Rhinovirus | Chang Epithelial Cells Murine Nasal Cells* | Apoptosis Internalization | [84, 129] |
| Cisplatin | HT29 Cells (Colon Carcinoma) | Apoptosis | [75] |

TABLE 1-continued

Ceramide-rich platform formation in biological systems.

| Stimulus | Cell type | Cellular outcome | Reference |
|---|---|---|---|
| Etoposide | Bovine Aortic Endothelial Cells* Human Coronary Artery Endothelial Cells* | Apoptosis | (Jacobi and Haimovitz-Friedman, unpublished) |
| Cytolytic T-cells | Murine Hepatocytes and Splenocytes* | Apoptosis | [119] |
| ROS | Peripheral Blood Neutrophils* | Apoptosis | [122] |
| Anti- FCγRII antibody | U937 (Monolytic Cells) | FCγRII phosphorylation | [91] |
| Anti-tumor ether lipid (ET-18-OCH$_3$) | Jurkat T Lymphocytes HL-60 Cells | Apoptosis | [130] |
| $Cu^{2+}$ treatment | Murine Hepatocytes* | Apoptosis | [80] |
| Ceramide (CD14 engagement) | Monocytes* | Innate immune | [65] |
| Endotoxin (LPS) | THP-1 Cells (Human Acute Promonocytic Leukemia) | TNFα production | [131] |
| Oxotremorine (Muscarinic type 1 receptor agonist) | Bovine Coronary Arterial Myocytes (CAMs)* | Production of cADPR and coronary artery constriction | [132] |

*primary cells

Combination of Antibiotics Targeting Gram Negative Bacteria and Anti-Ceramide Antibody has a Synergistic Therapeutic Effect CRPs mediate diverse disease pathologies. It has now been discovered that administering an anti-ceramide antibody, such as 2A2 or humanized 2A2, together with (although not necessarily simultaneously with) a broad-based antibiotic or an antibiotic targeting gram negative bacteria achieves significantly improved results in treating the enumerated diseases, compared to administering an anti-ceramide antibody alone. This new method of treatment is particularly effective in treating GI syndrome, GvHD, radiation disease and certain autoimmune diseases associated with GI damage, as well as other conditions that are also characterized by high levels of endothelial apoptosis and/or the formation of ceramide-rich platforms (CRP). Such diseases are listed in Table 2; all of these diseases are hereinafter collectively referred to as the "enumerated diseases."

TABLE 2

Role of ASMase and Ceramide-rich Platforms in Pathologic Conditions.

| | Disease | Reference |
|---|---|---|
| Vascular Disorders | PAF, TNF-induced pulmonary edema (ALI) | [67] |
| | γ radiation-induced tumor vascular dysfunction | [116] |
| | GI Syndrome | [78] |
| | Ischemic stroke | [133] |
| | Atherosclerosis | [134] |
| | Chronic heart failure | [135] |
| Metabolic Disorders | Wilson's disease | [80] |
| | Diabetes* | [136-138] |
| Cancer | Cancer chemotherapy (daunorubicin, cisplatin, gemcitabine) | [75, 76, 139, 140] |
| | γ radiation- and chemotherapy-induced side effects (GVHD, infertility) | [77, 118, 119] |

TABLE 2-continued

Role of ASMase and Ceramide-rich Platforms in Pathologic Conditions.

| | Disease | Reference |
|---|---|---|
| Infections | Pseudomonas aureginosa | [82] |
| | Rhinovirus | [84] |
| | Sindbis virus | [85] |
| | Neisseriae gonorrhoea | [81] |
| | Staphylococcus aureus | [141] |
| | Sepsis | [142] |
| Lung Diseases | Cystic fibrosis | [120] |
| | Emphysema* | [143] |
| Liver disease | Autoimmune hepatitis | [144] |
| Central Nervous System | Alzheimer's disease | [145] |

*Ceramide synthase has also been shown to be involved in generation of ceramide that mediates these pathologies It is important to emphasize that there are multiple pathways in a cell to make ceramide in different compartments. In an earlier publication, PCT/US08/62789, corresponding to U.S. Ser. No. 12/599,280, it was shown that ASMase-generated cell surface ceramide is responsible for causing radiation GI syndrome through damage to endothelial microvasculature (a hallmark of GI syndrome). Related in vivo studies showed that inhibiting or sequestering ASMase-generated cell surface ceramide by infusing anti-ceramide antibody following lethal radiation with a lethal 15 Gy inhibited ceramide-mediated raft clustering thereby abrogating endothelial apoptosis, and enhancing crypt survival. This thereby reduced GI stem cell lethality, and enhanced overall animal survival.

PCT/US08/62789 also disclosed results showing for the first time that ASMase-generated ceramide is required for acute GvHD. GvHD, the primary complication of hematopoietic stem cell transplantation, is a unique autoimmune-like disorder arising from the differentiation and activation of alloreactive donor T cells infused into an immunoablated host. In acute GvHD, recognition of alloantigens (major or minor mismatched) of the host by donor T cells initiates an adaptive immune response including incipient damage to host tissue and Type I cytokine (IFN-gamma and IL-2) generation. This results in CTL clonal expansion and activation, that along with a developing macrophage-dependent "cytokine storm" comprised of inflammatory cytokines (TNF-α. and IL-1β) induces apoptosis in a select set of target cells and consequent damage to associated target organs (liver, intestines and skin) (D. A. Wall, supra; G. F. Murphy, D. Whitaker, J. Sprent et al., *Am J Pathol* 138 (4), 983 (1991); D. A. Wall and K. C. Sheehan, *Transplantation* 57 (2), 273 (1994); G. R. Hill, W. Krenger, and J. L. Ferrara, *Cytokines Cell Mol Ther* 3 (4), 257 (1997); J. L. Ferrara, Bone Marrow Transplant 21 Suppl 3, S13 (1998); A. C. Gilliam, D. Whitaker-Menezes, R. Korngold et al., *J Invest Dermatol* 107 (3), 377 (1996)).

High-dose chemotherapy and radiation used in the treatment of many types of leukemia and lymphomas additionally kills rapidly dividing bone marrow stem cells, resulting in immunoablation and necessitating reconstitution of hematopoietic elements. GvHD is the major complication associated with such hematopoietic stem cell transplantation in cancer patients. PCT/US08/62789 also explains that ASMase-generated ceramide is required for acute GvHD and other T cell-mediated autoimmune diseases associated with an increase in pro-inflammatory cytokines, which diseases could be also be treated by the methods and compositions described herein There is a common thread of a requirement for ASMase-generated ceramide for radiation-induced lethality, GI syndrome, acute GvHD, and other T cell-mediated autoimmune diseases. In the studies described here, radiation lethality was used as a model for treating all of these diseases. Radiation GI Syndrome is the best defined GI pathology because it is rapid, highly reproducible and has a predictive in vivo assay, the Clonogenic Assay of Withers and Elkind, which defines the stem cell clonogenic response to injury in detail. GvHD and the Radiation GI Syndrome represent disease processes involving ASMase-mediated damage to the endothelial compartment coupled to the epithelial compartment (although the mechanism of activating ASMase differs between the two). In all of the radiation experiments described in FIGS. 1-3 male C57Bl/6 mice were irradiated with a lethal dose of 15.5 Gy subtotal body irradiation (SBI). In the experiments described in FIGS. 5-11 animals were irradiated with 15 Gy Total body irradiation, and in the FIG. 12 the animal was irradiated with 16 Gy SBI). Details of the Materials & Methods are set forth in Example 1.

4. Summary of Results and Specific Embodiments of the Invention

Figure 2:
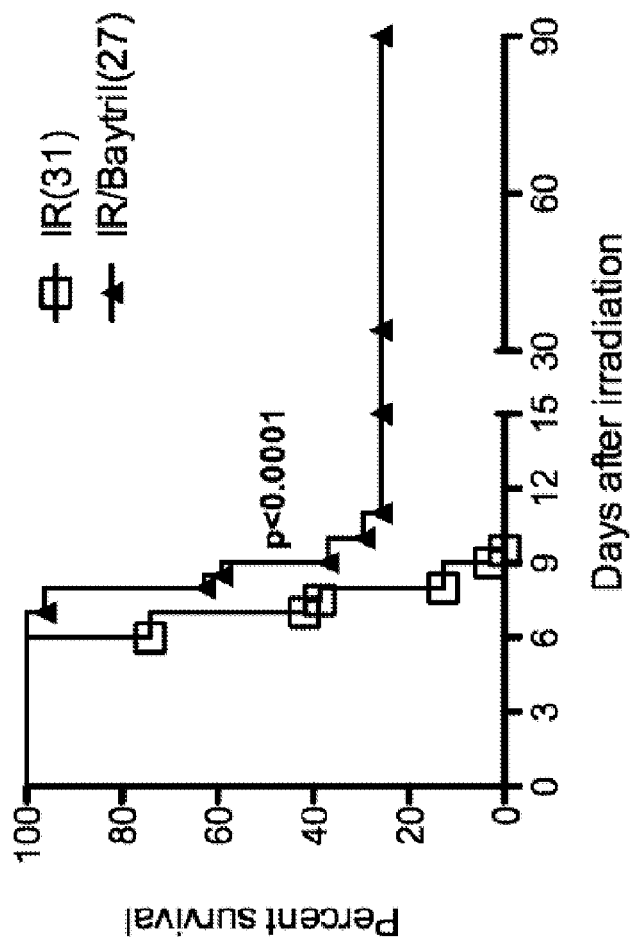
FIG. 2. Enrofloxacin (Baytril) administered 24 hours following 15.5 Gy SBI improves mouse survival. (A) Beginning 24 hours following exposure, irradiated C57BL/6 mice were given an estimated 3 mg/day of Baytril in their drinking water. Animal survival was calculated by the product limit Kaplan-Meier method. Necropsy of all animals that died in this study revealed denudation of GI mucosa indicative of the Radiation GI Syndrome.

As is shown in FIG. 1, when purified monoclonal 2A2 anti-ceramide antibody was administered by itself 24 hours following irradiation, mouse survival was significantly improved. Antibody therapy works best when delivered immediately or as soon as possible, preferably within 2 hours preceding irradiation. In another experiment, irradiated mice were treated with the quinolone antibiotic Enrofloxacin (hereinafter also "Baytril"), a fluoroquinolone with demonstrated efficacy against both Gram-negative and Gram-positive bacteria in both stationary and growth phases of bacterial replication. Mice were given free access to drinking water containing 0.57 mg/ml Baytril 24 hours following irradiation. Based upon the estimation of about 6 ml of drinking water consumed daily by 25 g C57BL/6 mice, the daily amount of Baytril consumed was about 3 mg/per animal per day. While 100% of untreated mice died by day 9, about 25% of mice treated with enrofloxacin survived for the 80 day duration of the study. FIG. 2.

Figure 3:
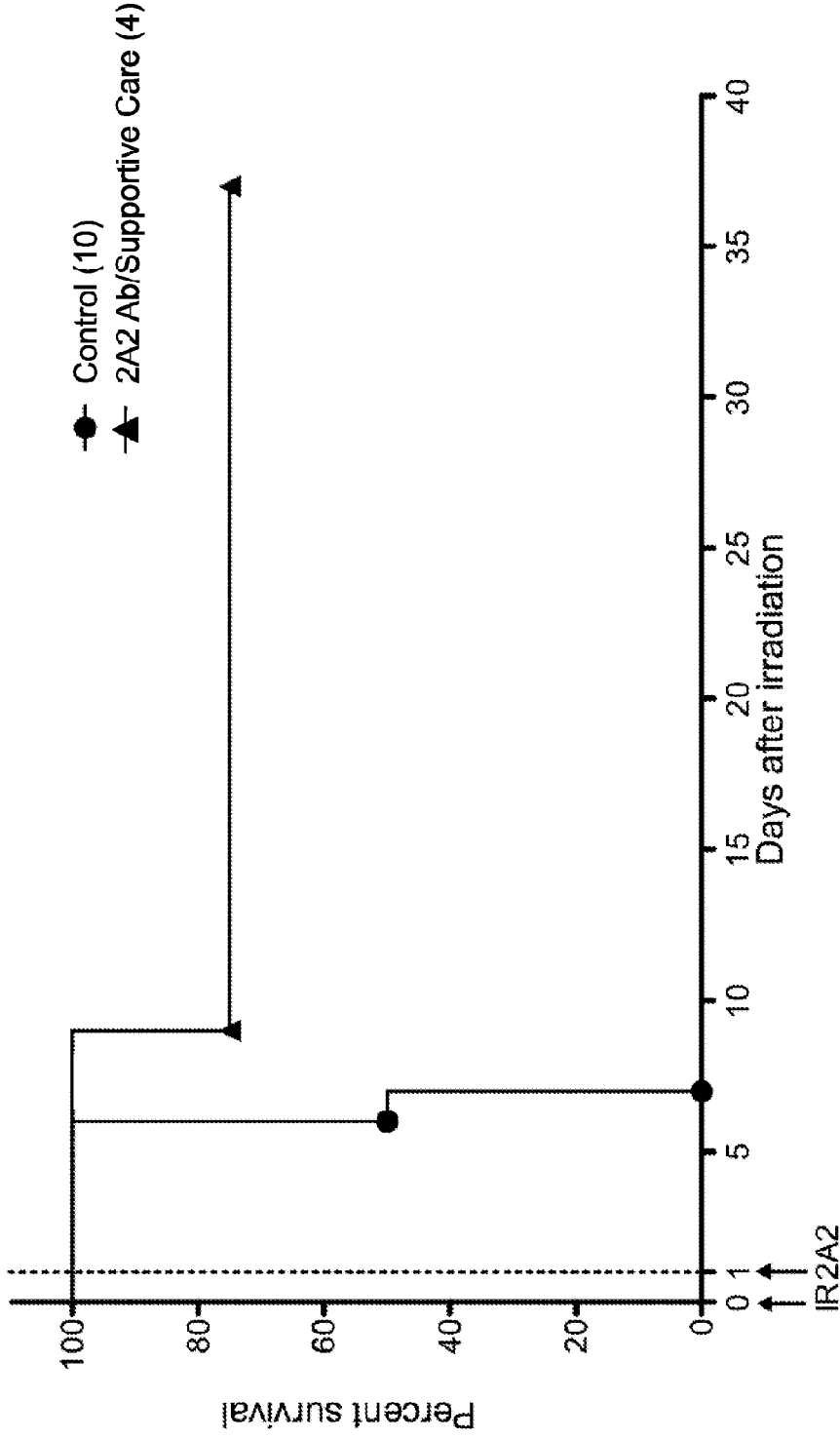
FIG. 3. Purified monoclonal 2A2 Ab and Baytril synergize to mitigate the GI Syndrome following 15.5 Gy SBI. (A) Purified 2A2 IgM (1000 µg) was administered by intravenous tail-vein injection 24 hours following irradiation, and an estimated 3 mg/day of Baytril was administered in drinking water. Animal survival was calculated by the product limit Kaplan-Meier method. Necropsy of all animals that died in this study revealed denudation of GI mucosa indicative of the Radiation GI Syndrome.

In a third experiment, both isolated and purified monoclonal 2A2 Ab and Baytril (3 mg/per animal per day) were administered 24 hours following irradiation. The results showed that this combination anti-ceramide antibody/antibiotic treatment had a synergistic effect in mitigating/treating GI Syndrome in irradiated mice. Without treatment, 100% of untreated mice died by day 6 post-irradiation. However, 75% of the mice treated with the 2A2 Ab and Baytril combination therapy survived for the duration of the study, an increase of more than 3 fold the survival achieved with either 2A2 or antibiotic alone. FIG. 3. Even better results are expected if the treatment is administered sooner.

Based on these results certain embodiments of the invention are directed to a method for preventing or treating or preventing an enumerated disease (GvHD, radiation disease, GI syndrome and certain autoimmune diseases) in an animal, by administering a therapeutically effective amount of an anti-ceramide antibody and either Baytril (or other quinolone antibiotic), or combinations of antibiotics selected from Table 1 or any broad spectrum antibiotic that is effective against Gram-negative antibiotic. The prophylactic and therapeutic agents described herein for combination therapy can be administered on the same or on consecutive days and they can be administered before or after radiation or graft transplant. Where treatment is not begun before radiation or transplantation, for example, therapy should be initiated as soon as possible after the enumerated disease is suspected or diagnosed. For mitigation of radiation disease, GI Syndrome, or GvHD, therapeutic agents should be delivered within either before radiation or transplantation or within the first 24 hours following radiation exposure or transplantation.

Antibiotics other than the quinolones are also expected to have a synergistic effect when administered together with an anti-ceramide antibody, and this can be tested using routine experimentation. Antibiotics that can be used in embodiments of the invention include quinolones (Baytril, ciprofloxacin), cephalosporins (cefepime, ceftazidine) or aminoglycosides (gentamicin, amikacin) that are therapeutically effective in mitigating radiation diseases like GI syndrome. Brook I, Elliot T B, Ledney G D, Shomaker M O, Knudson G B. Management of post-irradiation infection: lessons learned from animal models. Mil Med. 2004; 169:194-7.

Routine experimentation will determine the optimal therapeutically effective amount of antibiotic and anti-ceramide antibody to use. Prophylactically and therapeutically effective amounts of both the anti-ceramide antibody and the antibiotic are from about 0.1 mg/kg to about 100 mg/kg and from about 100 mg/kg to about 1000 mg/kg.

Fully human or humanized antibodies are preferred for a human subject. For antibodies, a therapeutic or prophylactic amount typically varies and can be an amount sufficient to achieve serum therapeutic agent levels typically of between about 1 microgram per milliliter and about 10 micrograms per milliliter in the subject. As is shown below, preincubation of Jurkat cells with 2A2 monoclonal anti-ceramide antibody (25-100 micrograms/mL) inhibited 8 Gy-induced apoptosis. In the context of the present invention, anti-ceramide antibodies are a type of neutralizing antibody that prevents ceramide-induced apoptosis. In addition to the monoclonal anti-ceramide antibody 2A2, we previously reported three other isotypes of monoclonal anti-ceramide antibodies, including 15D9 mAb, which is IgM, κ; and 1H4 and 5H9 mAbs, which are IgG3, κ antibodies (described in detail in published U.S. application Ser. No. 12/599,280; 2010/0239572). Any anti-ceramide antibody can be used in the present invention, including mono- and poly-clonal antibodies, and biologically active fragments or variants thereof.

The optimal therapeutic dose of an antibiotic can be determined with routine experimentation with guidance from the literature on treating radiation disease, GvHD and related symptoms. The management of established or suspected infection following exposure to radiation (characterized by neutropenia and fever) has been described. The patient that develops neutropenia after radiation is susceptible to irradiation damage to other tissues, such as the gastrointestinal tract, lungs and the central nervous system. These patients are typically treated with broad-spectrum empirical therapy with high doses of one or more of the enumerated antibiotics as soon as possible even before symptoms appear, but at least once fever is detected. The prophylactic and therapeutic amounts of the antibiotics administered to treat or prevent post-radiation GI damage are well known in the art and can be applied to embodiments of the present methods. Donnelly E H, Nemhauser J B, Smith J M, et al. (June 2010). "Acute radiation syndrome: assessment and management" *South. Med J.* 103(6): 541-PMID2071013; Baranov A E, Rozhdestvenskiĭ L M, Radiats Biol Radioecol. PMID: 18689253, 2008 May-June; 48(3): 287-302, The analytical review of the schemes of the acute radiation disease treatment used in experiment and in clinic; Brook I, Ledney D (1992). "Quinolone therapy in the management of infection after irradiation" *Crit Rev Microbiol:* 18235-46. The above-described antimicrobials include those that target Gram-negative aerobic organisms (i.e. Enterobacteriacae, *Pseudomonas*) that account for more than three-fourths of the isolates causing sepsis. Aerobic and facultative Gram-positive bacteria (mostly alpha-hemolytic streptococci) cause sepsis in about a quarter of the victims.

Quinolone antibiotics include Ciprofloxacin (Cipro, Pro-quin and others) Enoxacin (Penetrex and others) Gatifloxa-cin (Gatiflo, Tequin, Zymar and others) Gemifloxacin (Factive and others) Levofloxacin (Levaquin and others) Lomefloxacin (Maxaquin and others) Moxifloxacin (Avelox and others) Norfloxacin (Noroxin and others) Ofloxacin (Floxin and others) Prulifloxacin Sparfloxacin (Zagam and others) Trovafloxacin/Altrofloxacin (Trovan and others) Danofloxacin (A180 and others) Difloxacin (Dicural and others) Marbofloxacin (Orbax and others) Orbifloxacin (Zeniquin and others) Quinolones (older 'parent' class) Naldixic acid (NegGram and others) Cinoxacin (Cinobac and others)

Previous work also showed that statins (e.g., nystatin) had beneficial effects in reducing apoptosis in in vitro models of GvHD. Therefore certain other embodiments of the invention are directed to combination therapies of anti-ceramide antibody and antibiotics together with one or more statins. A description of statins for treating apoptosis is set forth in U.S. Ser. No. 12/599,280. The statins include, in alphabetical order (brand names vary in different countries)

| Statin | Brand Name | Derivation |
| --- | --- | --- |
| Atorvastatin | Lipitor, Torvast | Synthetic |
| Cerivastatin | Lipobay, Baycol. (Withdrawn from the market in August, 2001 | Synthetic |
| Fluvastatin | Lescol, Lescol XL | Synthetic |
| Lovastatin | Mevacor, Altocor, Altoprev | Fermentation-derived. Naturally-occurring compound. Found in oyster mushrooms and red yeast rice. |
| Mevastatin | — | Naturally-occurring compound, Found in red yeast rice. |
| Pitavastatin | Livalo, Pitava | Synthetic |
| Pravastatin | Pravachol, Selektine, Lipostat | Fermentation-derived |
| Rosuvastatin | Crestor | Synthetic |
| Simvastatin | Zocor Lipex | Fermentation-derived. (Simvastatin is a synthetic derivate of a fermentation product) |
| Simvastatin + Ezetimibe | Vytorin | Combination therapy |
| Lovastatin + Niacin extended-release | Advicor | Combination therapy |
| Atorvastatin + Amlodipine Besylate | Caudet | Combination therapy - Cholesterol + Blood Pressure |
| Simvastatin + Niacin extended-release | Simcor | Combination therapy |

In yet other embodiments, the ASMase inhibitor imipramine is included in the combination therapy. In U.S. Ser. No. 12/599,280 it was shown that ASMase-generated ceramide is required for both endothelial microvasculature damage and T-cell mediated killing. Inhibiting or sequestering ceramide generated by ASMase by administering anti-ceramide antibodies in vivo, reduced radiation-induced damage, and can be used to treat or prevent GI syndrome and GvHD. ASMase can be blocked with imipramine. In another embodiment antisense nucleic acids are administered together with antibiotics and anti-ceramide antibodies. Data supporting the inhibition of ASMase with imipramine or antisense nucleic acids was published in *The Journal of Biological Chemistry* (2005), 280, 26425-26434.

h2A2 Antibodies

Figure 7:
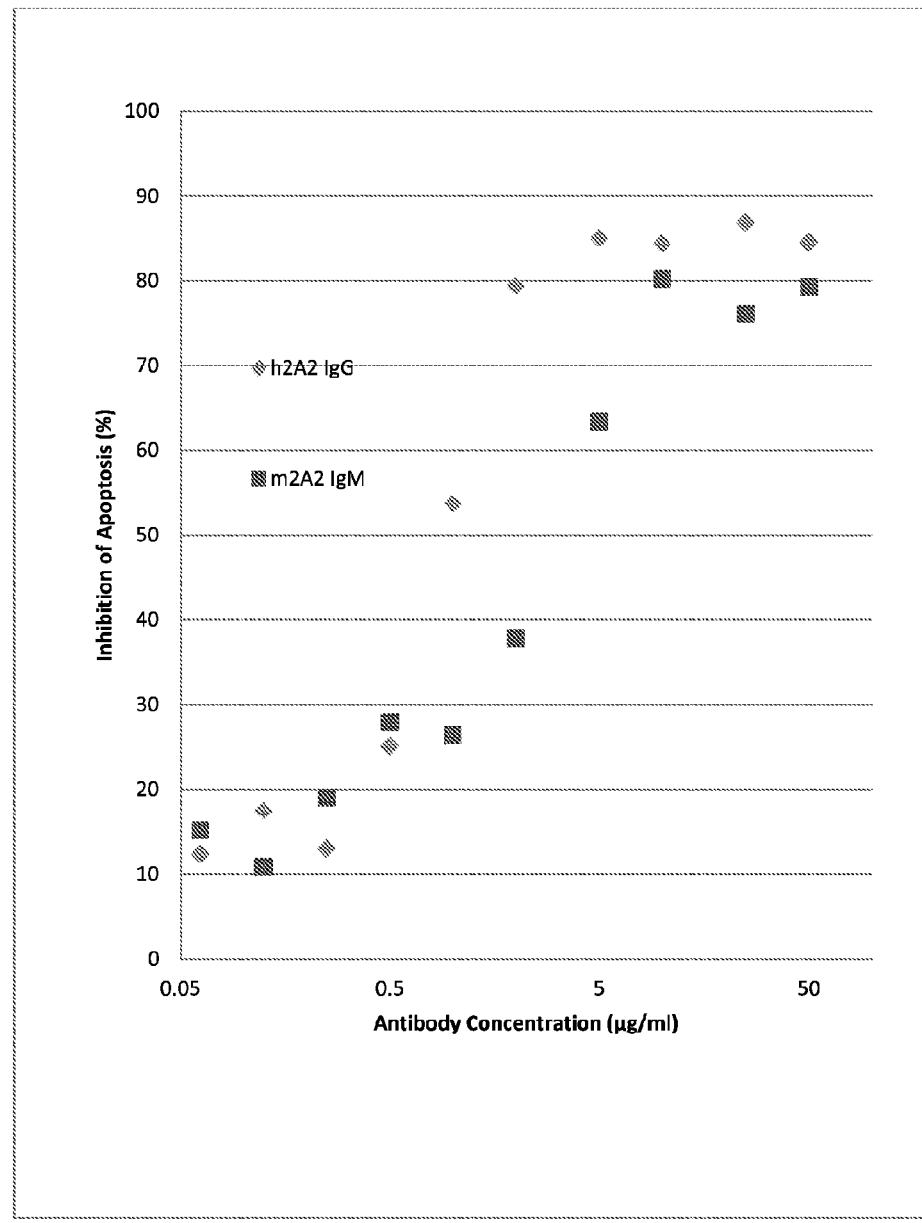
FIG. 7. h2A2 inhibits Jurkat cell apoptosis. Jurkat cells adjusted to $1 \times 10^6$ cell/ml in RPMI medium containing 10% FBS were administered h2A2 or m2A2 anti-ceramide antibody, and exposed to 10 Gy gamma irradiation. Cells were fixed after 16 hours, and apoptosis was quantified by Hoeschst bisbenzimide stain. Data is presented as percent inhibition of apoptosis of cells that did not receive Mab.

The humanization of the mouse 2A2 antibody is described in the Examples below. ELISA experiments revealed that h2A2 binds preferentially to ceramide (FIG. 5) and h2A2 binding to ceramide significantly exceeded that of the parent m2A2 antibody FIG. 6, and was comparable to the binding observed with commercially available anti-ceramide monoclonal IgM MID15B4 (Enzo Life Sciences), which antibody can also be used in embodiments of the invention. In vitro biologic activity of h2A2 IgG1 was determined using human Jurkat T lymphocytes that were exposed to 10 Gy ionizing radiation in the presence or absence of h2A2 IgG1. m2A2 IgM was used as a positive control in these experiments. Results indicated that h2A2 inhibited radiation-induced apoptosis of Jurkat cells in a dose-dependent manner. Importantly, inhibition of apoptosis is left-shifted compared to the parent murine 2A2 IgM, indicating that the h2A2 recombinant antibody is more potent. These data demonstrate that h2A2 is biologically active, and suggest that the recombinant humanized IgG1 will be effective in vivo. FIG. 7.

Figure 8:
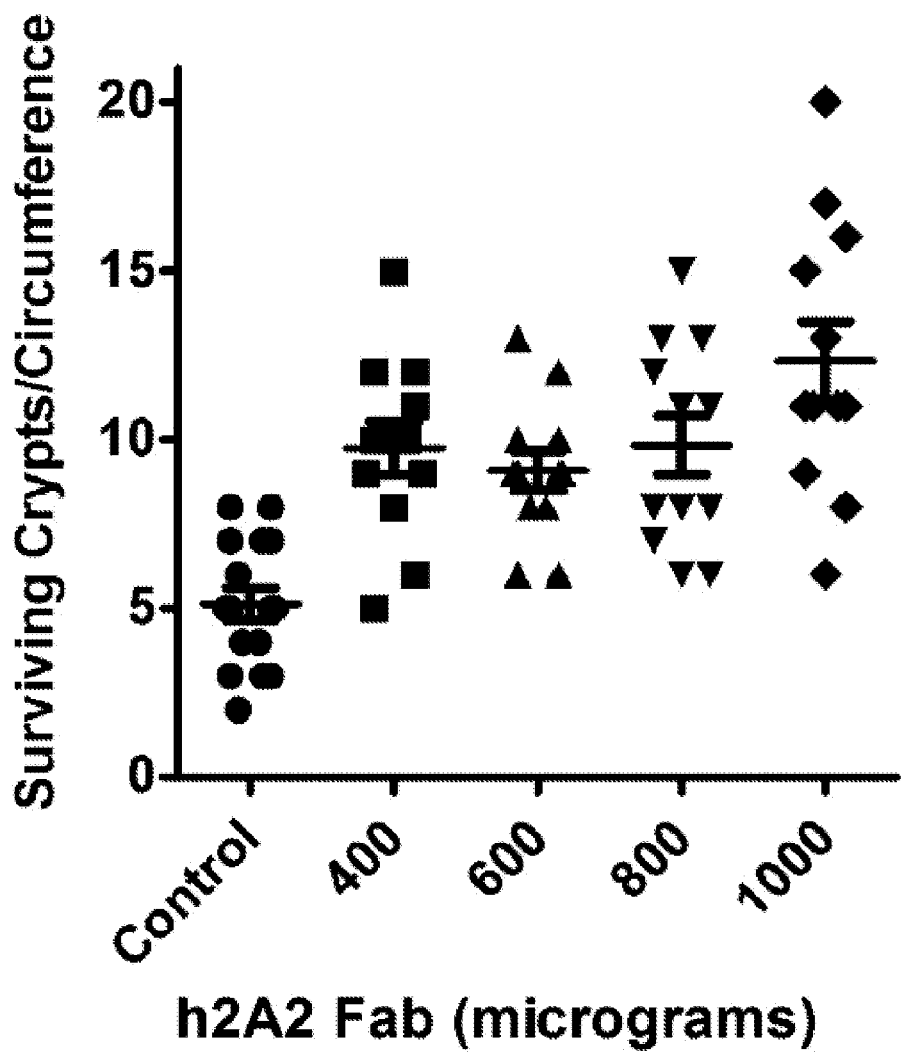
FIG. 8. h2A2 improves crypt stem cell survival following lethal radiation exposure. Male 6-10 week old C57Bl/6 mice were administered h2A2 monoclonal antibody 15 minutes prior to 15 Gy full body irradiation. Animals were sacrificed 3.5 days following irradiation, and tissues were processed for the crypt microcolony assay. Proximal jejunum sections were harvested for sectioning. Intestinal sections were stained with H&E, and surviving crypts were quantified FIG. 9. h2A2 protects crypt stem cells similarly as m2A2. Mice were administered h2A2 or m2A2 monoclonal antibody 15 minutes prior to 15 Gy full body irradiation, and the microcolony assay was performed as described.
Figure 9:
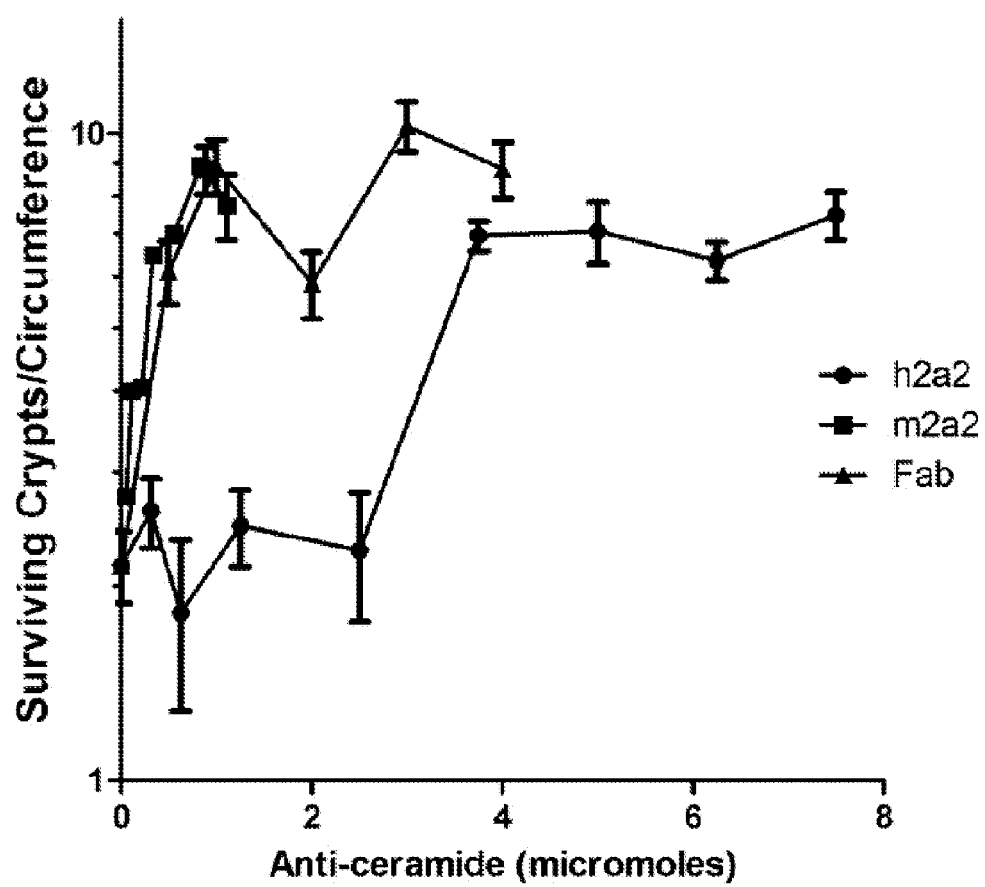
Figure 10:
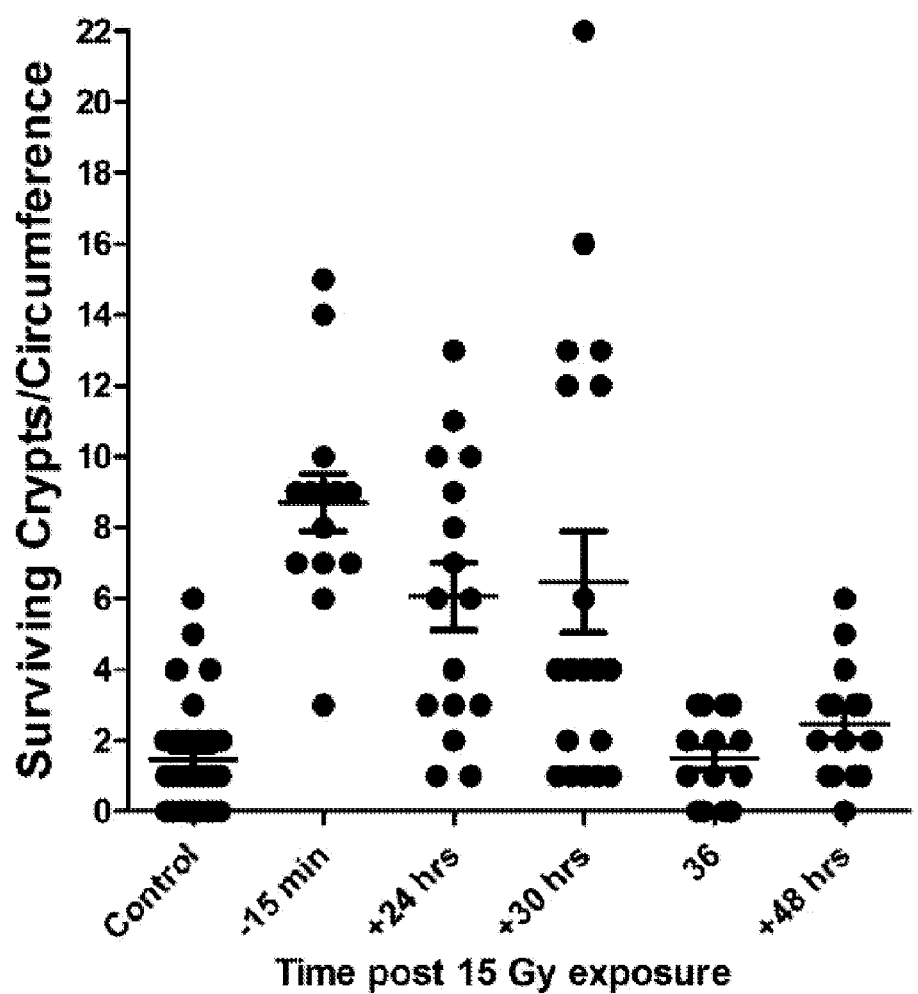
FIG. 10. h2A2 mitigates crypt stem cell death. Mice were administered h2A2 15 minutes prior to or up to 48 hours post 15 Gy full body irradiation, and the microcolony assay was performed as described.
Figure 11:
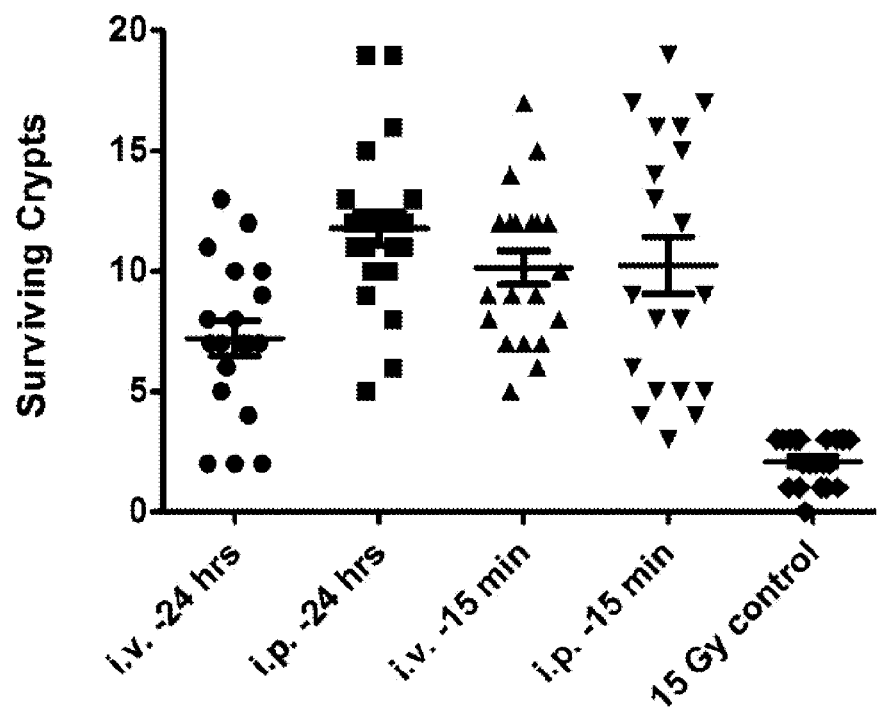
FIG. 11. h2A2 is an effective radioprotector or mitigator when administered via intraperitoneal injection. Mice were administered h2A2 15 minutes prior to or up to 48 hours post 15 Gy full body irradiation, and the microcolony assay was performed as described.

Increasing doses of h2A2 (50-1000 micrograms/mouse) were administered to C57BL/6 mice 15 minutes prior to 15 Gy total body irradiation. Direct comparison of the efficacy of h2A2 vs. m2A2 on surviving crypts indicated that h2A2 is equally effective as m2A2 as a prophylactic for the RGS. FIGS. 8-9. h2A2 was reported to be a highly effective mitigator of crypt lethality, showing efficacy even when administered as late as 30 hours post 15 Gy (FIG. 10) and it is as effective when administered IP as it is when it is administered IV (FIG. 11). IP injection may be preferable in disaster situations, as skilled healthcare workers required to administer a drug intravenously may not be readily available.

Figure 12:
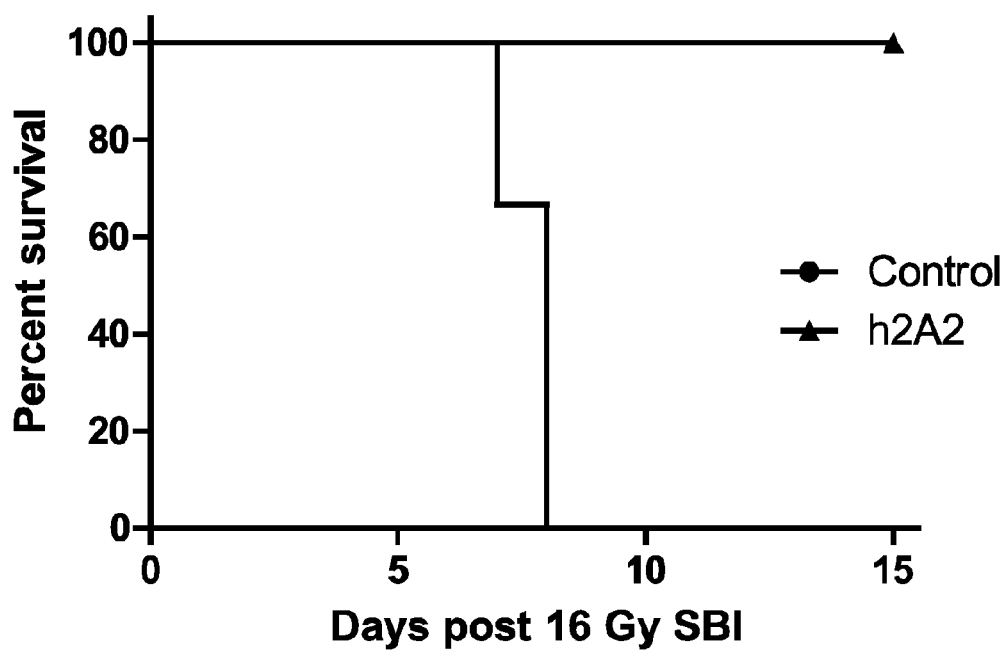
FIG. 12. h2A2 protects animals from the lethal RGS. Mice were administered h2A2 15 min prior to 15 Gy exposure. Animals were monitored for survival, and sacrificed when moribund. Kaplan-Meier actuarial survival analysis was performed. At least 5 mice were included in each group.
Figure 13A:
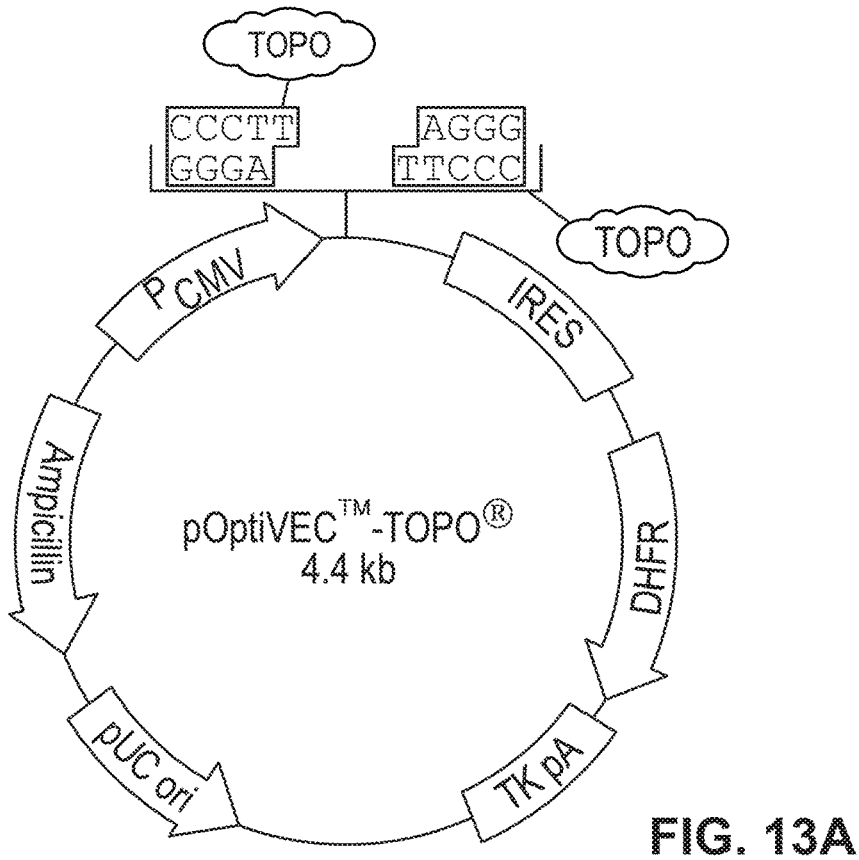
FIGS. 13A and 13B show the mammalian expression vector pOptiVEC and pcDNA 3.3, respectively.
Figure 13B:
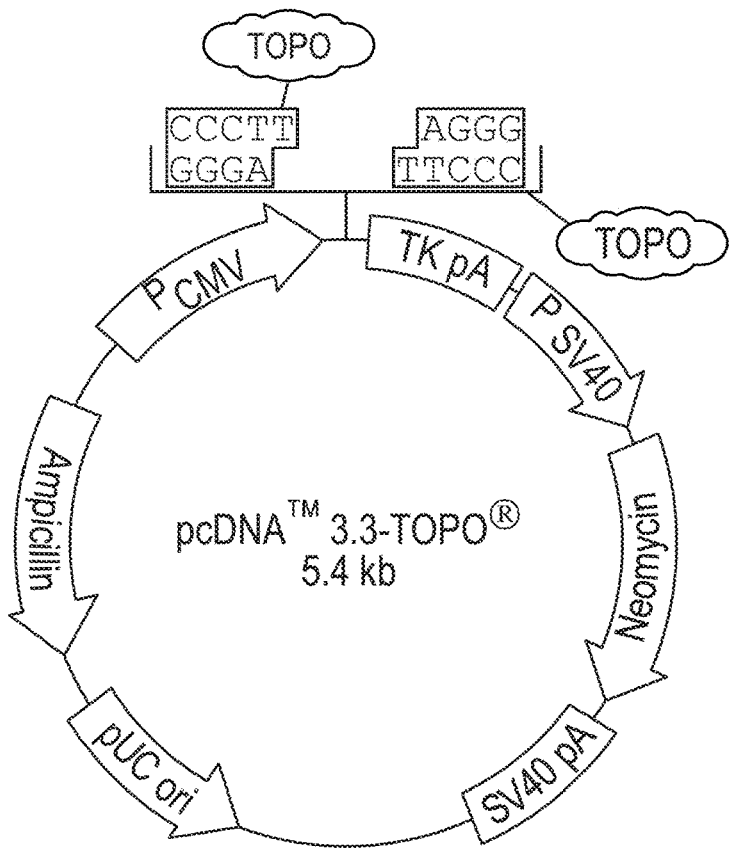

C57BL/6 mice exposed to 16 Gy sub-total body irradiation, were administered h2A2 15 minutes prior to radiation exposure, and survival was followed. 100% of animals treated with h2A2 survived at least 15 days while 100% of untreated animals died by day 8 post exposure, each dying with autopsy confirmed denudation of the GI mucosa and collapse of the crypt-villus units. FIG. 12. Therefore the h2A2 antibody or fragments thereof, are suitable for use in embodiments of the present invention. Other embodiments are directed to the h2A2 antibody itself or fragments or variants thereof.

Pharmaceutical Formulations

Certain embodiments are directed to pharmaceutical formulations of the enumerated antibiotics and antibodies in therapeutically or prophylactically effective amounts sufficient to prevent or treat the enumerated diseases in a subject. These pharmaceutical compositions are suitable for administration to a subject in need of prophylaxis or therapy. The subject is preferably a human but can be non-human as well. A suitable subject can be an individual who is suspected of having, has been diagnosed as having, or is at risk of developing one of the enumerated diseases. For the prevention or treatment of disease, the appropriate dosage of antibody and antibiotic will depend on the type of disease to be treated, the severity and course of the disease, whether the drug is administered for preventive or therapeutic purposes, previous therapy, the route of administration, the pharmacokinetics of the agent, the patient's clinical history and response to the new drugs (2A2 antibody, etc.) and the discretion of the attending physician.

As mentioned above, the amount of anti-ceramide antibody to be administered ranges from about 0.1 mg/kg to about 1000 mg/kg and the typical amount of antibiotic ranges from about 0.1 mg/kg to 1000 mg/kg. This amount typically varies and can be an amount sufficient to achieve serum therapeutic agent levels for each therapeutic agent that are typically of between about 1 microgram per milliliter and about 10 micrograms per milliliter in the subject. However, serum levels that elicit the desired response will vary. The therapeutic agents of the invention can be administered by one or more separate administrations, or by continuous infusion. For repeated administrations over several days or longer, depending on the condition, the treatment is sustained until the symptoms are sufficiently reduced or eliminated. The progress of this therapy is easily monitored by conventional techniques and assays, and may be used to adjust dosage to achieve a therapeutic effect.

Therapeutic compositions may contain, for example, such normally employed additives as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions typically contain 1%-95% of active ingredient, preferably 2%-70% active ingredient. The formulations may also contain more than one active compound as necessary for the particular indication being treated, preferably those with complementary activities that do not adversely affect each other. Such molecules are suitably present in combination in amounts that are effective for the purpose intended. For example, the 2A2 antibody and the antibiotic combinations could be formulated to further include a statin or imipramine.

Sustained-release preparations may also be prepared. Suitable examples of sustained release preparations include semipermeable matrices of solid hydrophobic polymers containing the antibodies or fragments, nystatin, imipramine or combinations thereof, which matrices are in the form of shaped articles, e.g., films, or microcapsule. Examples of sustained release matrices include, but are not limited to, polyesters, hydrogels (for example, poly (2-hydroxyethylmethacrylate), or poly (vinyl alcohol)), polylactides, copolymers of L-glutamic acid and y ethyl-L-glutamate, non-degradable ethylene-vinyl acetate, degradable lactic acid-glycolic acid copolymers such as the LUPRON DEPOT (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods.

The therapeutic agents may be present in the pharmaceutical compositions in the form of salts of pharmaceutically acceptable acids or in the form of bases or in amorphous form or in crystalline forms, including hydrates and solvates. Pharmaceutically acceptable salts of the therapeutic agents described herein include those salts derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate salts. Other acids, such as oxalic, while not in themselves pharmaceutically acceptable, may be employed in the preparation of salts useful as intermediates in obtaining pharmaceutically acceptable acid addition salts. Salts derived from appropriate bases include alkali metal (e.g., sodium and potassium), alkaline earth metal (e.g., magnesium), ammonium and $N^+(C_{1-4}$ alkyl$)_4$ salts. It is anticipated that some embodiment include the quaternization of any basic nitrogen-containing groups of the therapeutic agents disclosed herein. Water or oil-soluble or dispersible products may be obtained by such quaternization.

The therapeutic agents include all stereochemical forms of the therapeutic agents (i.e., the R and S configurations for each asymmetric center). Therefore, single enantiomers, racemic mixtures, and diastereomers of the therapeutic agents are within the scope of the invention. Also within the scope of the invention are steric isomers and positional isomers of the therapeutic agents. The therapeutic agents of some embodiments are also meant to include compounds which differ only in the presence of one or more isotopically enriched atoms. For example, therapeutic agents in which one or more hydrogen are replaced by deuterium or tritium, or the replacement of one or more carbons by $^{13}$C- or $^{14}$C-enriched carbon are within the scope of this invention.

The therapeutic agents of some embodiments are administered in a pharmaceutical composition that includes a pharmaceutically acceptable carrier, adjuvant, or vehicle. The term "pharmaceutically acceptable carrier, adjuvant, or vehicle" refers to a non-toxic carrier, adjuvant, or vehicle that does not destroy or significantly diminish the pharmacological activity of the therapeutic agent with which it is formulated. Pharmaceutically acceptable carriers, adjuvants or vehicles encompass any of the standard pharmaceutically accepted liquid carriers, such as a phosphate-buffered saline solution, water, as well as emulsions such as an oil/water emulsion or a triglyceride emulsion. Solid carriers may include excipients such as starch, milk, sugar, certain types of clay, stearic acid, talc, gums, glycols, or other known excipients. Carriers may also include flavor and color additives or other ingredients. The formulations of the combination of some embodiments may be prepared by methods well-known in the pharmaceutical arts and described herein. Exemplary acceptable pharmaceutical carriers have been discussed above.

The pharmaceutical compositions are preferably formulated for IV, intramuscular or subcutaneous administration. When antibiotics are administered separately from the antibody, it may be administered by any route known in the art for administering antibiotics, including oral administration.

These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Orally acceptable dosage forms (which are suitable for antibiotics administered separately from the antibodies), include solid forms such as capsules and tablets. Pharmaceutically compatible binding agents, and/or adjuvant materials can be comprised as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Solutions or suspensions used for parenteral, intradermal, IV, IM or subcutaneous application can comprise the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injection comprise sterile aqueous solutions (where water soluble) or dispersions and sterile powders for the extemporaneous preparation of sterile injectable solutions or dispersions. For intravenous administration, suitable carriers comprise physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the selected particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some cases, isotonic agents are included in the composition, for example, sugars, polyalcohols such as mannitol, sorbitol, or sodium chloride. Prolonged absorption of an injectable composition can be achieved by including in the composition an agent that delays absorption, for example, aluminum monostearate or gelatin.

Sterile injectable solutions can be prepared by incorporating the active compound in the specified amount in an appropriate solvent with one or a combination of ingredients enumerated above, as needed, followed by filtered sterilization. Generally, dispersions are prepared by incorporating the active compound into a sterile vehicle that contains a basic dispersion medium and other ingredients selected from those enumerated above or others known in the art. In the case of sterile powders for the preparation of sterile injectable solutions, the methods of preparation comprise vacuum drying and freeze-drying which yields a powder of the active ingredient plus any additional desired ingredient from a previously sterile-filtered solution thereof.

The compounds can also be prepared in the form of suppositories (e.g., with conventional suppository bases such as cocoa butter and other glycerides) or retention enemas for rectal delivery.

Biologically Active Fragments and Variants

"Biologically active fragments" of an anti-ceramide antibody as used herein, mean any fragment that retains binding affinity for ceramide. The fragments retain one or more CDR regions from the original antibody. CDRs are the sites of the antibody that bind to the antigen (i.e., in the present case ceramide) and in most cases are unique to that antibody. In order for a fragment to retain binding to the antigen, it would need to have at least one of these CDRs. Biologically active fragments may also contain minor variations provided that the variations in the amino acid sequence maintain at least 75%, more preferably at least 80%, 90%, 95%, and most preferably 99% sequence identity and the molecule retains its affinity for binding to ceramide.

"Variants" of an anti-ceramide antibody or fragment thereof include amino acid sequence modification(s) of the antibodies described herein that may, for example, improve the binding affinity and/or other biological properties of the antibody for the intended purpose of treating or mitigating an enumerated disease. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired affinity for ceramide. The amino acid alterations may be introduced in the subject antibody amino acid sequence at the time that sequence is made.

Antibodies

An "antibody" refers to an intact immunoglobulin or to an antigen-binding portion thereof that competes with the intact antibody for specific binding. Antigen-binding portions may be produced by recombinant DNA techniques or by enzymatic or chemical cleavage of intact antibodies. The term "recombinant human antibody", as used herein, is intended to include all human antibodies that are prepared, expressed, created or isolated by recombinant means, such as (a) antibodies isolated from an animal (e.g., a mouse) that is transgenic for human immunoglobulin genes, (b) antibodies expressed using a recombinant expression vector transfected into a host cell, (c) antibodies isolated from a recombinant, combinatorial human antibody library, and (c) antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V^H$ and $V_L$ sequences, may not naturally exist within the human antibody germline repertoire in vivo Antigen-binding portions include, inter alia, Fab, Fab', F(ab')$_2$, Fv, dAb, and complementarity determining region (CDR) fragments, single-chain antibodies (scFv), chimeric antibodies, diabodies and polypeptides that contain at least a portion of an immunoglobulin that is sufficient to confer specific antigen binding to the target ceramide Also included in the definition of antibodies is the SuperAntibody including those chemically conjugated to T15 peptide or genetically-engineered into a human IgG1 backbone (see Y. Zhao, D. Lou, J. Burkett and H. Kohler. Enhanced Anti-B-cell Tumor Effects with Anti-CD20 SuperAntibody. *J Immunotherapy*, 25: 57-62, 2002. The immunoglobulin subtype can be any subtype; typically IgG and IgM are used, but IgA, IgE etc. may also be effective.

An "immunoglobulin" is a tetrameric molecule. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as κ and λ light chains. Heavy chains are classified as M, δ, γ, α or ε, and define the antibody's isotype as IgM, IgD, IgG, IgA, and IgE, respectively.

The variable regions of each light/heavy chain pair form the antibody binding site such that an intact immunoglobulin has two binding sites. Immunoglobulin chains exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. See generally, Fundamental Immunology Ch. 7 (Paul, W., ed., 2nd ed. Raven Press, N.Y. (1989)). The term "epitope" means a determinant capable of specific binding to an antibody. Epitopes typically consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. From N-terminus to C-terminus, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991), or Chothia & Lesk J. Mol. Biol. 196:901 917 (1987); Chothia et al., Nature 342:878 883 (1989)).

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell. Monoclonal antibodies for use in the embodiments of the present invention are described below.

An Fab fragment is a monovalent fragment consisting of the VL, VH, CL and CH I domains; a F(ab')$_2$ fragment is a bivalent fragment comprising two Fab fragments linked by a disulfide bridge at the hinge region; a Fd fragment consists of the VH and CH1 domains; an Fv fragment consists of the VL and VH domains of a single arm of an antibody; and a dAb fragment (Ward et al., Nature 341:544 546, 1989) consists of a VH domain. A single-chain antibody (scFv) is an antibody in which a VL and VH regions are paired to form a monovalent molecules via a synthetic linker that enables them to be made as a single protein chain (Bird et al., Science 242:423 426, 1988 and Huston et al., Proc. Natl. Acad. Sci. USA 85:5879 5883, 1988). Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., Proc. Natl. Acad. Sci. USA 90:6444 6448, 1993, and Poljak, R. J., et al., Structure 2:1121 1123, 1994). One or more CDRs may be incorporated into a molecule either covalently or noncovalently to make it bispecific. Bispecific antibodies may also be used that have one combining site from an anti-ceramide antibody and a second site directed to a second antigen to improve targeting to T-cells etc. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a "bispecific" or "bifunctional" antibody has two different binding sites.

An "isolated antibody" is an antibody that (1) is not associated with naturally-associated components, including other naturally-associated antibodies, that accompany it in its native state, (2) is free of other proteins from the same species, (3) is expressed by a cell from a different species, or (4) does not occur in nature. An "isolated antibody," as used herein, is intended to refer to an antibody which is substantially free of other antibodies having different antigenic specificities. Moreover, an isolated antibody may be substantially free of other cellular material and/or chemicals. In one embodiment of the invention, a combination of "isolated" anti-ceramide antibodies having different specificities is combined in a well-defined composition. The embodiments of the invention use isolated antibodies.

The terms "human antibody" or "humanized antibody" includes all antibodies that have one or more variable and constant regions derived from human immunoglobulin sequences. Humanized antibodies are preferred for treating humans. A humanized antibody is one that is derived from a non-human species, in which certain amino acids in the framework and constant domains of the heavy and light chains have been mutated so as to avoid or abrogate an immune response in humans. Alternatively, a humanized antibody may be produced by fusing the constant domains from a human antibody to the variable domains of a non-human species. Examples of how to make humanized antibodies may be found in U.S. Pat. Nos. 6,054,297, 5,886,152 and 5,877,293. Methods for making the h2A2 antibody are found in the Examples.

The term "chimeric antibody" refers to an antibody that contains one or more regions from one antibody and one or more regions from one or more other antibodies.

Fragments or analogs of antibodies can be readily prepared by those of ordinary skill in the art following the teachings of this specification. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991).

Anti-Ceramide Monoclonal IgM Antibody

Figure 4:
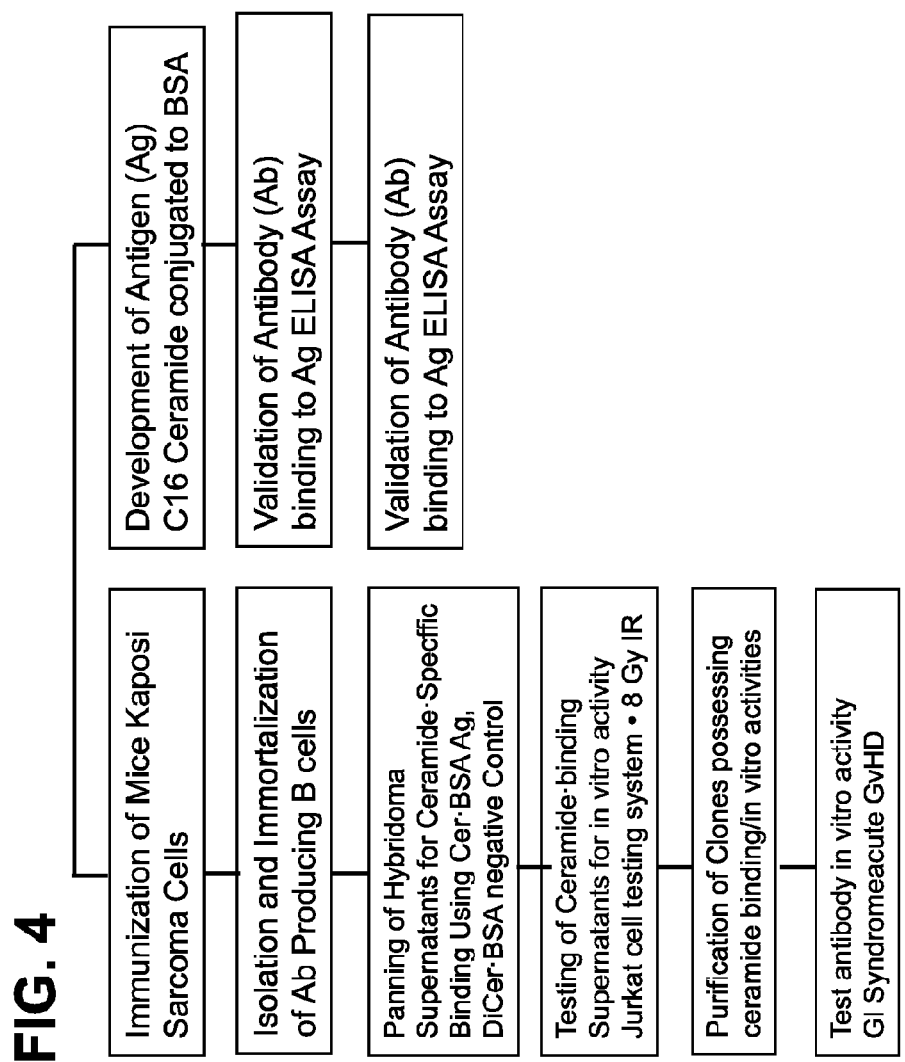
FIG. 4. A chart of the strategy used to generate novel anti-ceramide antibodies with potent in vivo activity.
Figure 5:
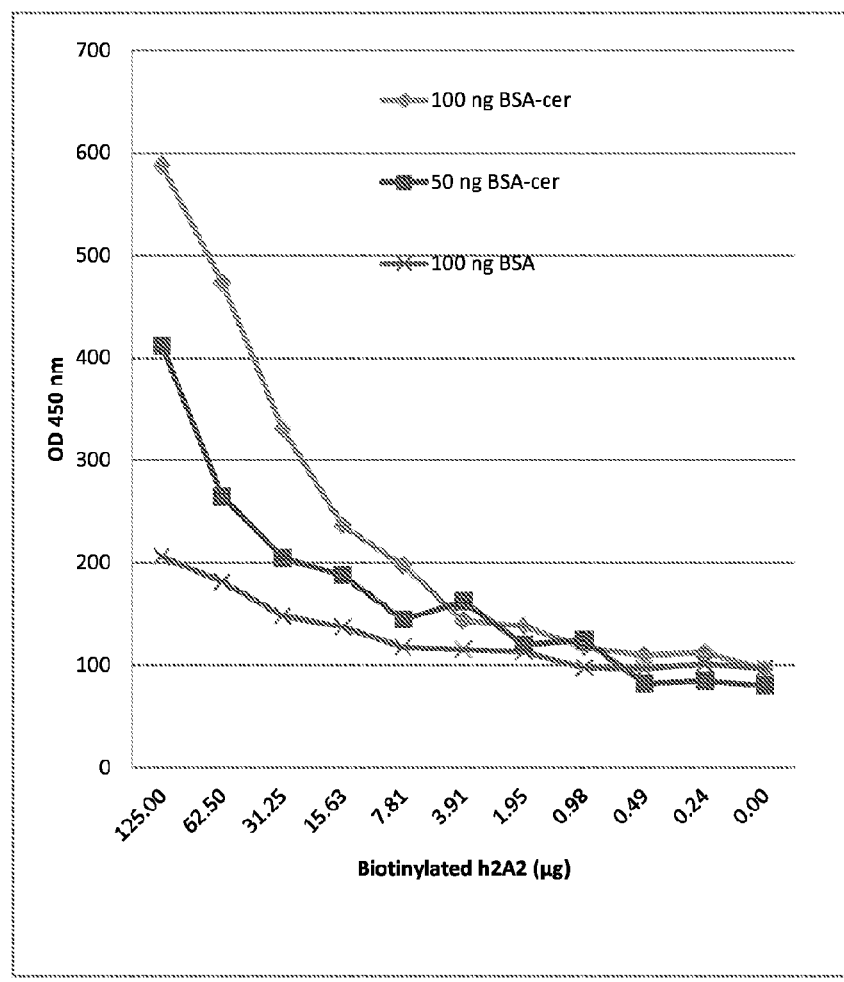
FIG. 5. h2A2 preferentially binds to ceramide. Maxisorp ELISA plates were coated overnight at 4° C. with BSA-conjugated to C16 carboxy-ceramide or BSA alone. Following blocking with 2 mg/ml non-fat milk solution, biotinylated h2A2 was added to the plate for 2 hrs at room temperature at the indicated concentration. Binding was determined following detection with HRP-conjugated streptavidin and quantification of signal by plate reader.
Figure 6:
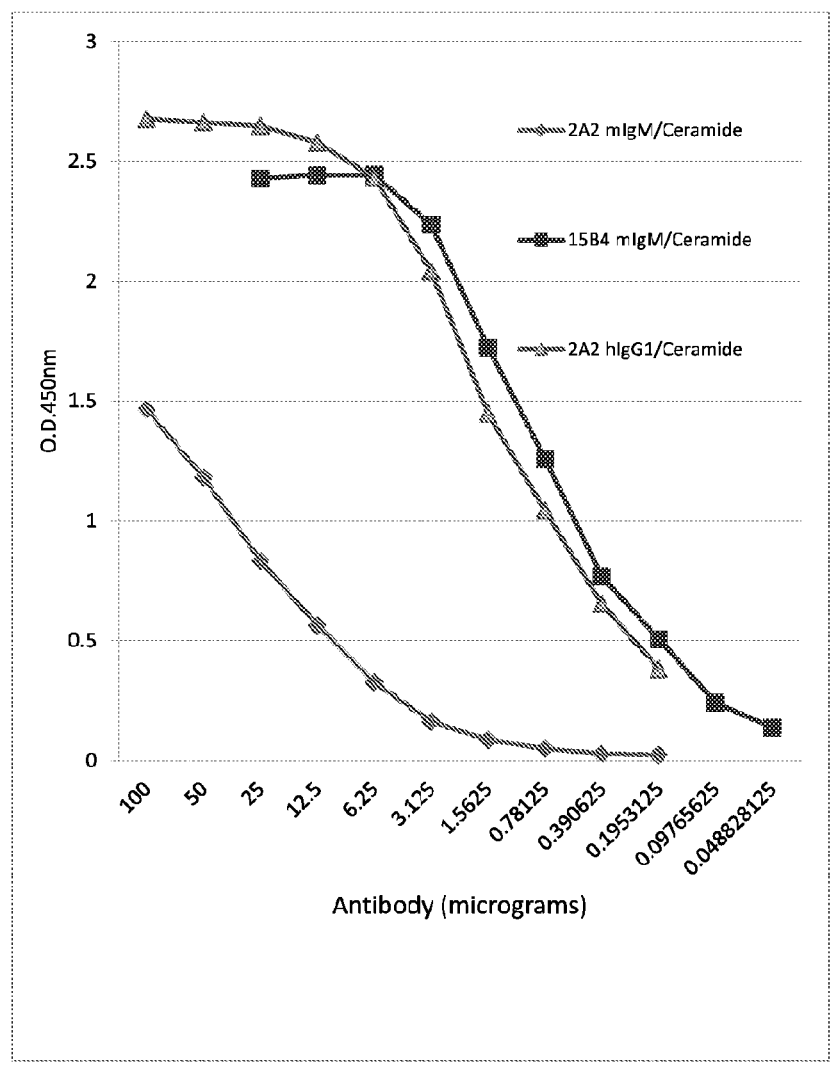
FIG. 6. h2A2 displays superior binding to ceramide than m2A2. ELISA was performed as described in FIG. 1. Binding of humanized IgG or mouse IgM was detected with anti-human HRP or anti-mouse HRP secondary antibody.

A flow chart of the strategy used to generate novel anti-ceramide antibodies with potent in vivo activity is shown in FIG. 4. The monoclonal antibodies, including 2A2, were made using methods known in the art and described in more detail in PCT/US08/62789. In order to make the antibody, a ceramide antigen was developed that was immunogenic enough to generate a strong antibody response from an inoculated host. BSA-conjugated ceramide was generated by synthesizing BSA-conjugated C16 fatty acid onto a sphingoid base. Validation of the antigen for antibody screening was performed by ELISA assay, in which decreasing amounts of antigen were fixed to a plate. After blocking each well, the plate was then incubated with anti-ceramide MID15B4 antibody (1:100) commercially available from Axxora LLC, San Diego, Calif. followed by horseradish peroxidase (HRP)-conjugated anti-mouse IgM. OD was assessed following administration of HRP substrate at 650 nm. The BSA-ceramide ELISA identified enhanced binding activity in supernatant #3673 following immunization of mice with Kaposi sarcoma cells. Binding activity remained following immortalization of antibody producing B cells enabling the isolation of monoclonal 2A2 IgM with anti-ceramide binding activity (not shown). Immunization with Kaposi sarcoma cells was intended to generate a strong immune response that would result in generation of a panel of antibody-producing B cells. The antibody-containing supernatant from the hybridomas generated from these B cells was then screened against the BSA-ceramide ELISA. Supernatants that tested positive in the assay were isolated, eventually resulting in purification of clone 2A2.

Purified monoclonal 2A2 antibody was isolated from supernatant #3673. ELISA revealed that the 2A2 mouse monoclonal IgM bound to BSA-ceramide. ELISA showed significantly more binding capacity of 2A2 vs. control IgM. Methods for humanizing the antibody and others are set forth in Example 1.

Certain other embodiments are directed to a composition comprising an anti-ceramide antibody, preferably humanized, such as h2A2, and an enumerated antibiotic such as a quinolone antibiotic. In other embodiments the Antibody/Antibiotic compositions optionally include (1) a statin in an amount that decreases circulating cholesterol levels thereby increasing the efficacy of the anti-ceramide antibody and/or (2) imipramine, an ASMase inhibitor presently used as an antidepressive agent. In some methods and compositions a mimotope that elicits an immune response in the subject causing the subject to form anti-ceramide antibodies, is used along with or instead of an anti-ceramide antibody.

Other monoclonal antibodies, made in mice that were immunized with BSA-ceramide, showed dose-dependent protective effects comparable to those of 2A2 when screened in a Jurkat cell apoptosis inhibition assay. These include 15D9, which is IgM, κ, and 1H4 and 5H9 mAbs, which are IgG3, κ.

Immunizing the host mice with Kaposi sarcoma cells generated effective anti-ceramide monoclonal antibodies with dramatic therapeutic effects as shown for example with the 2A2 antibody.

5. Examples

Example 1: Materials & Methods

The lethality of GI stem cell clonogens is best assessed by the number of crypts surviving at 3.5 days after radiation exposure, which decreases exponentially as the dose increases (C. S. Potten and M. Loeffler, Development 110 (4), 1001 (1990), H. R. Withers, Cancer 28 (1), 75 (1971), and J. G. Maj, F. Paris, A. Haimovitz-Friedman et al., Cancer Res 63, 4338 (2003)). Crypts that contain surviving stem cells proliferate at an accelerated rate, producing typical regenerative crypts that split or bud to generate new crypts, until the intestinal mucosa regains a normal architecture. Total body irradiation (1131) experiments in several mouse models have demonstrated that the number of surviving crypt stem cells after exposure to 8-12 Gy is usually sufficient to support a complete recovery of the mucosa. At higher doses, however, massive stem cell clonogen loss may lead to a near total collapse of the crypt-villus system, mucosal denudation and animal death from the GI syndrome. Autopsy studies of C57BL/6 mice exposed to TBI revealed that 25% of the mice exposed to 14 Gy and 100% of those exposed 15 Gy succumbed to the GI syndrome at 6.8.+/−0.99 days, predicting an LD50 for GI death between 14 and 15 Gy. A dose of 15 Gy was used in the experiments described herein. Subtotal was used for survival studies, as described in the next paragraph Male C57BL/6 mice (6-8 weeks old) were placed in a ventilated Plexiglas restrainer with head/forepaws and hind legs/tail covered by lead shield, and exposed to 15.5 Gy or 16 Gy subtotal body irradiation (SBI) (Philips MG-324 X-ray unit at a dose rate of 118.3 cGy/min, 50 cm source to skin distance). Purified 2A2 IgM (1000 μs) was administered by intravenous tail-vein injection 24 hours following irradiation. Beginning 24 hours following exposure, mice were given free access to drinking water containing 0.57 mg/ml Baytril, a fluoroquinolone with demonstrated efficacy against both Gram-negative and Gram-positive bacteria in both stationary and growth phases of bacterial replication. Based upon the estimation of 6 ml of drinking water consumed daily by 25 g C57BL/6 mice, daily Baytril consumption is estimated at 3 mg/day.

Radiation and Tissue Preparation

TBI (total body irradiation) was used only for protection studies, SBI for mitigation studies was delivered with a Shepherd Mark-I unit (Model 68, SN643) operating $^{137}$Cs sources. The dose rate was 2.12 Gy/min. To collect small intestinal samples, mice were sacrificed by hypercapnia asphyxiation, and 2.5 cm segments of the proximal jejunum were obtained at 2 cm from the ligament of Trietz. Tissue samples were fixed by overnight incubation in 4% neutral buffered formaldehyde and embedded in paraffin blocks. To evaluate intestinal tissue responses to radiation, transverse sections of the full jejunal circumference (5 micrometers thick) were obtained by microtomy from the paraffin blocks, adhered to polylysine-treated slides and deparaffinized by heating at 90 degrees Celsius for 10 minutes and at 60 degrees Celsius for 5 minutes, followed by two xylene washes for 5 minutes, and stained with hematoxylin and eosin according to a standard protocol. To determine the causes of death after TBI, autopsies were performed within 60 min of animal death or when terminally-sick animals displaying an agonal breathing pattern were sacrificed by hypercapnia asphyxiation. Tissue specimens were collected from all animals, fixed in formaldehyde, and stained with hematoxylin.

Survival of Mice after Irradiation and Designation of Autopsy Findings.

Actuarial survival of animals was calculated by the product limit Kaplan-Meier method. Terminally sick animals displaying an agonal breathing pattern were sacrificed by hypercapnia asphyxiation and evaluated by necropsy to determine cause of death. Intestinal specimens were fixed in formaldehyde, and stained with hematoxylin. GI damage can be diagnosed as the cause of death when the small intestines display denuded mucosa with nearly no villae or crypts apparent or when the mucosa display limited mucosal repair (Kaplan, E. L. and P. Meier, Nonparametic estimation from incomplete observations. J of the American Statistical Association, 1958. 53: p. 457-48; Rotolo, J. A., et al., Bax and Bak do not exhibit functional redundancy in mediating radiation endothelial apoptosis in the intestinal mucosa. Int J Radiat Oncol Biol Phys, 2008. 70(3): p. 804-15).

Example 2

Methods for Making Humanized 2A2 Antibody

Methods for making monoclonal mouse 2A2 Antibody are described in PCT/US08/62789.

Humanization of 2A2 was performed to generate a humanized 2A2 (h2A2) monoclonal antibody by the CDR grafting method. Usually, rodent antibodies can be immunogenic to human and cause very serious side effects including the HAMA (human anti-mouse antibodies) response or anaphylactic shock. With this CDR grafting approach, CDR loops that make up the antigen-binding site of the mouse Mab are grafted into corresponding human framework regions. Initially, the variable light and heavy chain sequences of m2A2 were determined. To do so, m2A2 hybridoma cells were harvested by centrifugation and total RNA was extracted from cells. Total RNA was used for cDNA synthesis, and V-region genes of 2A2 were isolated using standard primer sets.

To identify human VL and VH homologous to those of 2A2, the variable regions of 2A2 were compared with variable regions of human germline sequences using the VBASE online database. As a result, two human germline VL and VH sequences were found. The following sequences are variable heavy (VH) and light chain (VL) of mouse 2A2, human germline sequences, and homologous regions of these mouse and human sequences:

```
SEQ ID NO. 1: Mouse 2A2 Variable Heavy Chain (VH)
FR1                           CDR1     FR2              CDR2
EVQLQQSGTVLARPGASVKMSCKASGYTFTNYWMHWVKQRPVQGLEWIGAIYPGDSDTSYNQKFKG FR3                                 CDR3    FR4
KAKLTAVTSTSTAFMELSSLTNEDSAVYYCTGLYYGYDWGQGTTLTVSS SEQ ID NO. 2: Human germline 2A2 Variable Heavy Chain of the 2A2
antibody
FR1                           CDR1     FR2              CDR2
```

```
QVQLVQSGAEVKKPGASVKVSCKASGYTFTSYYMHWVRQAPGQGLEWMGIINPSGGSTSYAQKFQGRV

TMTRDTSTSTVYMELSSL

FR3                              FR4
RVTMTRDTSTSTVYMELSSLRSEDTAVYYCARWGQGTTVTVSS

SEQ ID NO. 9: Homologous regions of mouse 2A2 Variable Heavy Chain
of the 2A2 antibody; with human germline 2A2 Very Heavy Chain
  FR1                       CDR1   FR2              CDR2
  +VQL QSG  +  +PGASVK+SCKASYTFT +Y+MH WV+Q P QGLEW+G   I P    TSY

QKF+G

FR3                            CDR3   FR4
    + +T   TSTST +MELSSL  +ED+AVYYC           WGQGTT+TVSS

SEQ ID NO. 3: Mouse 2A2 Variable Light Chain (VL)
FR1                   CDR1             FR2            CDR2
DVLMTQTPLTLSVTIGQPASISCKSSQSLIDSDGKTFLNWLLQRPGQSPKRLIYLVSKLDS FR3                        CDR3     FR4
GVPDRFTGSGSGTDFTLKISRVEAEDLGLYYCWQGTHFPYTFGGGTKLEIK SEQ ID NO. 4: Human germline 2A2 Variable Light (VL)
FR1                   CDR1             FR2            CDR2
DVVMTQSPLSLPVTLGQPASISCRSSQSLVYSDGNTYLNWFQQRPGQSPRRLIYKVSNWDS FR3                        CDR3     FR4
GVPDRFSGSGSGTDFTLKISRVEAEDVGVYYCMQGTHWPTFGQGTKLEIKR SEQ ID NO. 10: Homologous regions of mouse 2A2 Variable LIGHT Chain
of the 2A2 antibody; with human germline 2A2 Very Heavy Chain
FR1                   CDR1             FR2            CDR2
DV+MTQ+PL+L VT+GQPASISC +SSQSL+ SDG T+LN W  QRPGQSP+RLIY   VS  DS FR3                         CDR3     FR4
GVPDRF+GSGSGTDFTLKISRVEAED+G+YYC  QGTH+P T FG GTKLEIKR
```

**Note that "+" means that the amino acid at that spot is not identical but has some similar properties.

The selected 2A2 VH sequence was found to be most homologous to the human V gene 1-46 from the VH1 family and human J gene JH6. The selected 2A2 VL sequence was found to be most homologous with the human V gene A1 from the Vk2 family and human J gene Jk2. m2A2 CDR sequences were grafted into these VL and VH, such that the synthesized sequences each contained three mouse CDRs in the selected human framework sequences. As 2A2 Mab is originally a murine IgM, the h2A2 Mab was converted to the IgG1 format. IgG1 Mabs have many benefits over IgM, including that IgG1 is the most abundant Mab in serum (9 mg/ml), its half-life (21 days) is longer than any other antibody, and, currently, many commercial therapeutic antibodies are IgG1 format. To construct humanized 2A2 IgG1 in a mammalian expression vector, pOptiVEC and pcDNA 3.3 (Invitrogen) vectors were used. The following is a brief vector map.

The vector contains the human cytomegalovirus (CMV) immediate-early promoter/enhancer for high-level expression of recombinant proteins in a wide range of mammalian cells. The human variable light and heavy chains containing the three CDRs of mouse 2A2 were synthesized and linked to the human constant light and heavy chain by PCR. The humanized 2A2 light chain was cloned into pcDNA3.3 TOPO, and humanized 2A2 heavy chain was cloned into the pOptiVEC TOPO antibody expression vector. Sequences of human 2A2 IgG1 have be shown below. The first amino acid (Arginine, red color shading) of human constant light chain was deleted during construction of whole humanized light chain. After construction of these human 2A2 Ab expression vectors, the DNA plasmids were co-transfected into CHO-derived, DHFR-negative DG44 cells to create a stable cell line that produces 2A2 hIgG1 antibody.

```
SEQ ID NO. 5: HUMANIZED 2A2 HEAVY CHAIN DNA SEQUENCE
ATGGACTGGACCTGGAGGGTCTTCTGCTTGCTGGCTGTAGCTCCAGGTGCTCACT

CCCAGGTGCAGCTTGTGCAGTCTGGGGCTGAGGTGAAAAAGCCTGGGGCTTCAGTGA

AGGTGTCCTGCAAGGCTTCTGGCTACACCTTTACCAACTACTGGATGCACTGGGTAAG

ACAGGCGCCTGGACAGGGTCTGGAATGGATGGGCGCTATTTATCCTGGAGATAGTGA

TACTAGCTACAACCAGAAGTTCAAGGGCCGGGTCACAATGACTCGAGACACATCCACC

AGCACTGTCTACATGGAGCTCAGCAGCCTGAGAAGTGAGGACACTGCGGTCTATTACT

GTGCACGCCTTTACTACGGCTACGACTGGGGCCAAGGCACCACTGTCACAGTCTCCT
```

-continued

CAGCCAGCACGAAGGGCCCATCGGTCTTCCCCCTGGCACCCTCCTCCAAGAGCAC

CTCTGGGGGCACAGCGGCCCTGGGCTGCCTGGTCAAGGACTACTTCCCCGAACC

GGTGACGGTGTCGTGGAACTCAGGCGCCCTGACCAGCGGCGTGCACACCTTCCC

GGCTGTCCTACAGTCCTCAGGACTCTACTCCCTCAGCAGCGTGGTGACCGTGCCC

TCCAGCAGCTTGGGCACCCAGACCTACATCTGCAACGTGAATCACAAGCCCAGC

AACACCAAGGTGGACAAGAAAGTT*GAGCCCAAATCTTGTGACAAAACTCACACATG*

*CCCACCGTGCCC*AGCACCTGAACTCCTGGGGGGACCGTCAGTCTTCCTCTTCCCC

CCAAAACCCAAGGACACCCTCATGATCTCCCGGACCCCTGAGGTCACATGCGTG

GTGGTGGACGTGAGCCACGAAGACCCTGAGGTCAAGTTCAACTGGTACGTGGAC

GGCGTGGAGGTGCATAATGCCAAGACAAAGCCGCGGGAGGAGCAGTACAACAG

CACGTACCGTGTGGTCAGCGTCCTCACCGTCCTGCACCAGGACTGGCTGAATGGC

AAGGAGTACAAGTGCAAGGTCTCCAACAAAGCCCTCCCAGCCCCCATCGAGAAA

ACCATCTCCAAAGCCAAAGGGCAGCCCCGAGAACCACAGGTGTACACCCTGCCC

CCATCCCGGGATGAGCTGACCAAGAACCAGGTCAGCCTGACCTGCCTGGTCAAA

GGCTTCTATCCCAGCGACATCGCCGTGGAGTGGGAGAGCAATGGGCAGCCGGAG

AACAACTACAAGACCACGCCTCCCGTGCTGGACTCCGACGGCTCCTTCTTCCTCT

ACAGCAAGCTCACCGTGGACAAGAGCAGGTGGCAGCAGGGGAACGTCTTCTCAT

GCTCCGTGATGCATGAGGCTCTGCACAACCACTACACGCAGAAGAGCCTCTCCC

TGTCCCCGGGTAAA*TGA*

First underline: leader sequence
First Italic:: variable heavy chain sequence
Second Underline: CH1 sequence
Second Italic: hinge sequence
Third underline: CH2 and CH3 sequence

SEQ ID NO. 6 AMINO ACID SEQUENCE OF HUMANIZED 2A2 HEAVY CHAIN

MDWTWRVFCLLAVAPGAHS[QVQLVQSGAEVKKPGASVKVSCKASGYTFTNYWM

HWVRQAPGQGLEWMGAIYPGDSDTSYNQKFKGRVTMTRDTSTSTVYMELSSLRSEDTAVYY

CARLYYGYDWGQGTTVTVSS]ASTKGPSVFPLAPSSKSTSGGTAALGCLVKDYFPEPVT

VSWNSGALTSGVHTFPAVLQSSGLYSLSSVVTVPSSSLGTQTYICNVNHKPSNTKVD

KKV*EPKSCDKTHTCPPCP*APELLGGPSVFLFPPKPKDTLMISRTPEVTCVVVDVSHED

PEVKFNWYVDGVEVHNAKTKPREEQYNSTYRVVSVLTVLHQDWLNGKEYKCKVS

NKALPAPIEKTISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHEALHNHYTQ

KSLSLSPG

First underline: leader sequence
Bracketed sequence = variable heavy chain sequence
NYWMH (SEQ ID NO: 11) = CDR
LYYGYD (SEQ ID NO: 12) = CDR
Second Underline: CH1 sequence
Second Italic: hinge sequence
Third underline: CH2 and CH3 sequence SEQ ID NO. 7: HUMANIZED 2A2 LIGHT CHAIN DNA SEQUENCE
ATGAGGCTCCCTGCTCAGCTCCTGGGGCTGCTAATGCTCTGGGTCCCAGGATCCA

GTGGGG*ATGTTGTGATGACCCAATCTCCACTCTCTTTGCCGGTTACCCTTGGACAACC*

*AGCCTCCATCTCTTGCAAGTCAAGTCAGAGCCTCATAGATAGTGATGGAAAGACATTTT*

*TGAATTGGTTCCAACAGAGGCCAGGCCAGTCTCCAAGGCGCCTAATCTATCTGGTGTC*

-continued

```
TAAACTGGACTCTGGAGTCCCTGACAGGTTCTCTGGCAGTGGATCAGGGACAGATTTC

ACTCTGAAAATCAGCAGAGTGGAGGCTGAGGATGTGGGAGTTTATTATTGCTGGCAAG

GTACACATTTTCCGTACACGTTCGGACAGGGGACCAAGCTGGAAATAAAACGGACGGT

GGCTGCACCATCTGTCTTCATCTTCCCGCCATCTGATGAGCAGTTGAAATCTGGAACT

GCCTCTGTTGTGTGCCTGCTGAATAACTTCTATCCCAGAGAGGCCAAAGTACAGTGGA

AGGTGGATAACGCCCTCCAATCGGGTAACTCCCAGGAGAGTGTCACAGAGCAGGACA

GCAAGGACAGCACCTACAGCCTCAGCAGCACCCTGACGCTGAGCAAAGCAGACTACG

AGAAACACAAAGTCTACGCCTGCGAAGTCACCCATCAGGGCCTGAGTTCGCCCGTCA

CAAAGAGCTTCAACAGGGGAGAGTGTTAA
```

First Underline: leader sequence
First italics: variable light chain sequence
Second underline: Deleted amino acid
Second italics: constant kappa light chain sequence SEQ ID NO. 8: AMINO ACID SEQUENCE OF HUMANIZED 2A2 LIGHT CHAIN
MRLPAQLLGLLMLWVPGSSG[DVVMTQSPLSLPVTLGQPASISCKSSQSLIDSDGKT

FLNWFQQRPGQSPRRLIYLVSKLDSGVPDRFSGSGSGTDFTLKISRVEAEDVGVYYC

WQGTHFPYTFGQGTKLEIK]R*TVAAPSVFIFPPSDEQLKSGTASVVCLLNNFYPREAKVQ*

*WKVDNALQSGNSQESVTEQDSKDSTYSLSSTLTLSKADYEKHKVYACEVTHQGLSSPVTKS*

*FNRGEC*

First underlined sequence = leader sequence
Brackets = variable light chain sequence
KSSQSLIDSDGKTFLNW (SEQ ID NO: 13) = CDR sequence
LVSKLDS (SEQ ID NO: 14) = CDR sequence
WQGTHFPYT (SEQ ID NO: 15) = CDR sequence
Second underlined sequence = deleted amino acid
First Italics: constant kappa light chain sequence To obtain cell lines that produce high levels of antibody, a pool of stably-transfected cells were selected by performing two rounds of selection using CD OptiCHO medium and CD OptiCHO medium with 500 µg/ml of Geneticine, followed by MTX genomic amplification selection and two rounds of single cell clonal selection in semi-solid media in a 96-well plate. Antibody expression levels were screened by ELISA assay quantification and selected h2A2IgG1-CHO cell (G3A10, C5G6 and D5F11) lines were slowly scaled up.

In vitro production of h2A2 IgG1 recombinant antibody was performed in OptiCHO serum free media using a hollow fiber bioreactor. Expansion of this clone allowed bulk-production and purification of h2A2 IgG1 in the hollow-fiber system. Purification of recombinant IgG from concentrated harvest was performed using standard Protein-A/G affinity chromatography. Antibody was eluted, buffer exchange was performed and antibody in phosphate-buffered saline was frozen in aliquots at a concentration of 3 mg/ml for further analysis. To date, we have purified over 50 milligrams of recombinant h2A2 for evaluation in vitro and in vivo.

To confirm the binding affinity of h2A2 to ceramide, performed a series of ELISA assays were performed using $C_{16}$ ceramide covalently bound to either bovine serum albumin (BSA) or ovalbumin (OVA) via a linkage at the terminal end of the fatty acid subunit of ceramide. Briefly, h2A2 was biotinylated, and antibody binding to microplates coated with BSA- or OVA-conjugated C16 ceramide was determined using horse-radish peroxidase labeled streptavidin. Experiments revealed that h2A2 bound C16 ceramide in a dose-dependent manner.

What is claimed is:

1. A method for treating radiation disease associated with gastrointestinal (GI) damage in a subject, comprising administering a therapeutically effective amount of an anti-ceramide antibody, or an antigen-binding fragment thereof, and a therapeutically effective amount of a fluoroquinolone antibiotic that is effective against Gram-negative bacteria,
   wherein the anti-ceramide antibody or antigen-binding fragment comprises a variable heavy ($V_H$) domain and a variable light ($V_L$) domain,
      wherein the $V_H$ domain comprises the $V_H$ CDR1 sequence, the $V_H$ CDR2 sequence and the $V_H$ CDR3 sequence of SEQ ID NO:1 or SEQ ID NO: 6; and
      the $V_L$ domain comprises the $V_L$ CDR1 sequence, $V_L$ CDR2 sequence and $V_L$ CDR3 sequence of SEQ ID NO:3 or SEQ ID NO: 8; and
wherein the fluoroquinolone antibiotic is selected from the group consisting of Enrofloxacin (Baytril), Ciprofloxacin (i.e., Cipro and Proquin), Enoxacin (i.e., Penetrex), Gatifloxacin (i.e., Gatiflo, Tequin and Zymar), Gemifloxacin (i.e., Factive), Levofloxacin (i.e., Levaquin), Lomefloxacin (i.e., Maxaquin), Moxifloxacin (i.e., Avelox), Norfloxacin (i.e., Noroxin), Ofloxacin (i.e., Floxin), Prulifloxacin, Sparfloxacin (i.e., Zagam), Trovafloxacin, Alatrofloxacin (i.e., Trovan), Danofloxacin (i.e., A180), Difloxacin (i.e., Dicural), Marbofloxacin (i.e., Orbax), Orbifloxacin (i.e., Zeniquin), Flumequine, Fleroxacin, Pefloxacin, Rufloxacin, Balofloxacin, Grepafloxacin, Pazufloxacin, Temafloxacin, Tosufloxacin, Besifloxacin, Clinafloxacin, Sitafloxacin, Ibafloxacin, Pradofloxacin, and Sarafloxacin.

2. The method of claim 1, wherein the fluoroquinolone antibiotic is selected from the group consisting of Enrofloxacin (Baytril), Ciprofloxacin (i.e., Cipro and Proquin), Gatifloxacin (i.e., Gatiflo, Tequin and Zymar), Levofloxacin (i.e., Levaquin), Lomefloxacin (i.e., Maxaquin), Moxifloxacin (i.e., Avelox), Norfloxacin (i.e., Noroxin), Ofloxacin (i.e., Floxin), Prulifloxacin, Sparfloxacin (i.e., Zagam), Danofloxacin (i.e., A180), Difloxacin (i.e., Dicural), Marbofloxacin (i.e., Orbax), Orbifloxacin (i.e., Zeniquin), Flumequine, Fleroxacin, Pefloxacin, Rufloxacin, Balofloxacin, Grepafloxacin, Pazufloxacin, Temafloxacin, Besifloxacin, Clinafloxacin, Sitafloxacin, Ibafloxacin, Pradofloxacin, and Sarafloxacin.

3. The method of claim 1, wherein the antibody is a monoclonal antibody.

4. The method of claim 3, wherein the monoclonal antibody is secreted by a hybridoma derived from spleen cells of a subject immunized with Kaposi Sarcoma (KS) cells.

5. The method of claim 1, wherein the antibody is a h2A2 humanized mouse monoclonal antibody.

6. The method of claim 5, wherein the antibody is 2A2 IgG or IgM humanized mouse monoclonal antibody.

7. The method of claim 1, wherein the antibody and the antibiotic are administered either before or after irradiation of the subject.

8. The method of claim 1, wherein the effective amount of the anti-ceramide antibody is from about 0.1 mg/kg to about 100 mg/kg, and the effective amount of the antibiotic is from about 0.1 mg/kg to about 100 mg/kg.

9. The method of claim 1, wherein the antigen-binding fragment is an scFv.

* * * * *